United States Patent
Lentzsch et al.

(10) Patent No.: US 12,018,069 B2
(45) Date of Patent: *Jun. 25, 2024

(54) METHODS AND COMPOSITIONS FOR IMAGING AMYLOID DEPOSITS

(71) Applicant: The Trustees of Columbia University in the City of New York, New York, NY (US)

(72) Inventors: Suzanne Lentzsch, Bronx, NY (US); Akiva Mintz, Paramus, NJ (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/265,206

(22) Filed: Feb. 1, 2019

(65) Prior Publication Data

US 2020/0002410 A1 Jan. 2, 2020

Related U.S. Application Data

(63) Continuation-in-part of application No. 16/021,168, filed on Jun. 28, 2018, now Pat. No. 11,382,974.

(60) Provisional application No. 62/753,410, filed on Oct. 31, 2018.

(51) Int. Cl.
| | | |
|---|---|---|
| C07K 16/18 | (2006.01) |
| A61B 5/055 | (2006.01) |
| A61K 51/10 | (2006.01) |
| C07B 59/00 | (2006.01) |

(52) U.S. Cl.
CPC .......... *C07K 16/18* (2013.01); *A61K 51/1018* (2013.01); *A61B 5/055* (2013.01); *C07B 59/008* (2013.01); *C07K 2317/51* (2013.01)

(58) Field of Classification Search
CPC .......... C07K 16/18; C07K 2317/24; C07K 2317/51; A61K 51/1018; A61K 49/0004; A61B 5/055; A61B 6/037; G01N 2800/7047; G01N 2800/52; C07B 59/008

See application file for complete search history.

(56) References Cited

U.S. PATENT DOCUMENTS

| | | |
|---|---|---|
| 6,787,140 B1 | 9/2004 | Schenk |
| 7,256,273 B2 | 8/2007 | Basi et al. |
| 7,927,594 B2 | 4/2011 | Rosenthal et al. |

(Continued)

FOREIGN PATENT DOCUMENTS

| | | |
|---|---|---|
| AU | 2003262458 A1 | 12/2003 |
| EP | 2730659 A2 | 5/2014 |

(Continued)

OTHER PUBLICATIONS

Wall JS et al. Radioimmunodetection of amyloid deposits in patient with AL amyloidosis. Blood, 2010, 116(13):2241-2244. (Year: 2010).*

(Continued)

*Primary Examiner* — Adam Weidner
*Assistant Examiner* — Laura Ann Essex
(74) *Attorney, Agent, or Firm* — McCormick, Paulding & Huber PLLC

(57) ABSTRACT

Methods and diagnostic compositions for detection of amyloid deposits using a chimeric (e.g., mouse-human) antibody or antigen-binding fragment thereof linked to a detectable label are disclosed.

31 Claims, 9 Drawing Sheets

Specification includes a Sequence Listing.

(56) References Cited

U.S. PATENT DOCUMENTS

| | | | |
|---|---|---|---|
| 8,105,594 | B2 | 1/2012 | Solomon et al. |
| 8,195,594 | B1 | 6/2012 | Bryce |
| 8,404,815 | B2 | 3/2013 | Schenk et al. |
| 8,591,894 | B2 | 11/2013 | Holtzman et al. |
| 8,642,044 | B2 | 2/2014 | Schenk et al. |
| 9,310,383 | B2 | 4/2016 | Goure et al. |
| 11,382,974 | B2 | 7/2022 | Lentzsch |
| 2002/0086847 | A1 | 7/2002 | Chain |
| 2005/0019330 | A1 | 1/2005 | Schenk |
| 2009/0232733 | A1 | 9/2009 | O'Nuallain et al. |
| 2009/0297439 | A1* | 12/2009 | Comoglio .......... A61K 51/1027 424/1.49 |
| 2010/0080806 | A1 | 4/2010 | Liu et al. |
| 2010/0150906 | A1 | 6/2010 | Pfeifer et al. |
| 2010/0322932 | A1 | 12/2010 | Solomon et al. |
| 2011/0177066 | A1 | 7/2011 | Schenk |
| 2013/0295082 | A1 | 11/2013 | Garidel et al. |
| 2016/0024197 | A1 | 1/2016 | Burbidge et al. |
| 2016/0243230 | A1 | 8/2016 | Wall et al. |
| 2016/0264637 | A1 | 9/2016 | Romeuf et al. |
| 2018/0148504 | A1 | 5/2018 | O'Shannessy et al. |
| 2020/0181246 | A1 | 6/2020 | Jones et al. |

FOREIGN PATENT DOCUMENTS

| | | |
|---|---|---|
| ES | 2436112 T3 | 12/2013 |
| JP | 2009-530374 A | 8/2009 |
| JP | 2017528449 A | 9/2017 |
| KR | 20150002879 A | 1/2015 |
| RU | 2475500 C2 | 2/2013 |
| RU | 2498999 C2 | 11/2013 |
| WO | 9960024 A1 | 11/1999 |
| WO | 1999060024 A1 | 11/1999 |
| WO | 0072880 A2 | 12/2000 |
| WO | 2007108756 A1 | 9/2007 |
| WO | 2008011348 A2 | 1/2008 |
| WO | 2008052933 A2 | 5/2008 |
| WO | 2013151762 A1 | 10/2013 |
| WO | 2016032949 A1 | 3/2016 |
| WO | 2016187546 A1 | 11/2016 |
| WO | 2017184973 A1 | 10/2017 |
| WO | 2019006062 A1 | 1/2019 |

OTHER PUBLICATIONS

Merlini G. Al amyloidosis: from molecular mechanisms to targeted therapies. Hematology Am Soc. Hematol. Educ. Program. 2017 Dec. 8, 2017(1): 1-12. (Year: 2017).*

Endocardium, Wikipedia entry retrieved Mar. 11, 2022, en.wikipedia. org/wiki/Endocardium, 2 pages. (Year: 2022).*

Comenzo RL et al. Managing systemic light-chain amyloidosis. J. National Comprehensive Cancer Network, 2007, 5, 179-187. (Year: 2007).

Lin CY et al. Toxic human islet amyloid polypeptide (h-IAPP) oligomers are intracellular, and vaccination to induce anti-toxic oligomer antibodies does not prevent h-IAPP-induced beta-cell apoptosis in h-IAPP transgenic mice. Diabetes, 2007, 56, 1324-1332. (Year: 2007).

Study of Chimeric Fibril-Reactive Monoclonal Antibody 11-1 F4 in Patients with AL Amyloidosis, ClinicalTrials.gov, Identifier: NCT02245867, first posted Sep. 22, 2014, retrieved from internet Dec. 9, 2019. (Year: 2014).

Entzsch, Suzanne. Phase 1a/1 b study of 11-1 F4 mAb for the treatment of AL amyloidosis, 2015 NIH Grant# 1 RO 1 FD005110-01, retrieved from Grantome.com on Dec. 9, 2019. (Year: 2019).

Anger AL et al. Results of phase I study of chimeric fibril-reactive monoclonal antibody 11-1 F4 in patients with AL amyloidosis. Blood, 2015, 126(23), 188, Meeting abstract 653. (Year: 2015).

Guidance for Industry: Estimating the maximum safe starting dose in initial clinical trials for therapeutics in adult healthy volunteers. US Dept. of Health and Human Service, Food and Drug Administration (FDA), Center for Drug Evaluation and Research (CDER), Jul. 2005, 30 pages. (Year: 2005).

Buss SJ et al. Longitudinal left ventricular function for prediction of survival in systemic light-chain amyloidosis. J. Amer. College Cardiology, 2012, 60(12), 1067-76. (Year: 2012).

International Search Report dated Jan. 13, 2020 for PCT/US19/58720.

Edwards et al. "Analysis of the Phase 1 a/b Study of Chimeric Fibril-Reactive Monoclonal Antibody 11-1 F4 in Patients with AL Amyloidosis," Blood, Dec. 1, 2016 (Dec. 1, 2016), vol. 128, No. 22, p. 643. entire document.

Edwards et al. "Final Analysis of the Phase 1 a/b Study of Fibril-Reactive Monoclonal Antibody 11-1 F4 (CAEL-101) in Patients with AL Amyloidosis," Columbia University Medical Center, Dec. 10, 2017 (Dec. 10, 2017), pp. 1-24. Retrieved from the Internet: www.caelumbio.com/wp-content/uploads/2017/02/11-1 F4-ASH-Presentation-2017-12-Dec2017.pdf> on Nov. 28, 2018 (Nov. 28, 2018). entire document.

Pun et al. "Prognostic and Added Value of Two-Dimensional Global Longitudinal Strain for Prediction of Survival in Patients with Light Chain Amyloidosis Undergoing Autologous Hematopoietic Cell Transplantation," Journal of the American Society of Echocardiography, Oct. 27, 2017 (Oct. 27, 2017), vol. 31, Iss. 1, pp. 64-70. entire document.

Solomon et al. "Therapeutic Potential of Chimeric Amyloid-reactive Monoclonal Antibody 11-1F4," Clinical Cancer Research, Sep. 1, 2003 (Sep. 1, 2003), vol. 9, Iss. 10, pp. 3831s-3838s. entire document.

Leng et al. "958: Improvement in Global Longitudinal Strain (GLS) Correlates with NT-Probnp Response in Patients with Cardiac Amyloidosis Treated on a Phase 1 b Study of Anti-Amyloid Mab Cael-101," 2018 ASH Annual Meeting, San Diego Convention Center, Nov. 2, 2018 (Nov. 2, 2018), pp. 1-3. Retrieved from the Internet: ash.confex.com/ash/2018/webprogram/Paper118464.html> on Nov. 28, 2018 (Nov. 28, 2018). entire document.

International Search Report dated Sep. 24, 2018 for PCT Application No. PCT/US2018/039905.

International Search Report dated Dec. 26, 2018 for PCT Application No. PCT/US2018/043374.

Merlini G. et al., Molecular mechanisms of amyloidosis, N. Engl. J. Med., 2003, vol. 349, Issue 6, pp. 583-596.

Tuzovic M. et al., Cardiac Amyloidosis: Diagnosis and Treatment Strategies, Curr Oncol Rep., 2017, vol. 19, Issue 7, p. 46.

Riechmann L. et al., Reshaping human antibodies for therapy, Nature, 1988, vol. 332, Issue 6162, pp. 323-327.

Vajdos F.F. et al., Comprehensive Functional Maps of the Antigenbinding Site of an Anti-ErbB2 Antibody Obtained with Shotgun Scanning Mutagenesis, J. Mol. Biol., 2002, vol. 320, pp. 415-428.

De Pascalis R. et al., Grafting of "abbreviated" complementarity-determining regions containing specificity-determining residues essential for ligand contact to engineer a less immunogenic humanized monoclonal antibody, J Immunol., 2002, vol. 169, Issue 6, pp. 3076-3084.

Russian Search Report for corresponding Russian Application No. 2020108100 dated Oct. 7, 2020.

Australian Examination Report for corresponding Australian Application No. 2018290898 dated Nov. 12, 2020.

Wall, Jonathan, "Radioimmunodetection of amyloid deposits in patients with AL amyloidosis", Blood, 2010, vol. 116, No. 13, pp. 2241-2244.

Japanese Office Action dated Dec. 15, 2020 for corresponding Japanese Application No. 2019-572403.

Edwards C. V. et al. Interim analysis of the phase 1a/b study of chimeric fibril-reactive monoclonal antibody 11-1F4 in patients with AL amyloidosis // Amyloid.—2017.—V. 24.—No. sup1.—p. 58-59. [Найдено Mar. 6, 2020], URL: www.tandfonline.com/doi/abs/10.1080/13506129.2017.1292900.

Examination Report in corresponding Australian Application No. 2018311688 dated Feb. 16, 2021.

Desport, E., et al. "Al-Amyloidosis," vol. 18, No. 4 (2014) pp. 36-50.

(56) References Cited

OTHER PUBLICATIONS

Lavatelli, et al., Biochemical markers in early diagnosis and management of systemic amyloidoses. Clin. Chem. Lab Med. 2014, 52 (11):1517-1531. (Year: 2014).
Columbian Office Action and its English translation dated Dec. 6, 2021 for corresponding Columbian Application No. 20200000260.
Van Doren et al. Nonchemotherapy treatment of immunoglobulin light chain amyloidosis. Acta Haematol. 2020, 143:373-380. (Year:2020).
Extended European Search Report dated Apr. 23, 2021 for corresponding European Application No. 18 840 642.5.
Indian First Examination Report and its English translation dated Mar. 28, 2022 for corresponding Indian Application No. 201947053227.
Zhou et al. "Receptor-Mediated Abeta Amyloid Antibody Targeting to Alzheimer's Disease Mouse Brain." Molecular Pharmaceutics. vol. 8, No. 1. pp. 280-285. Dec. 9, 2010.
Moghimi et al. "High Efficiency Ex Vivo Gene Transfer to Primary Murine B Cells Using Plasmid or Viral Vectors." J Genet Syndr Gene Ther. vol. 2, No. 103. Apr. 3, 2013. 10 pages. doi:10.4172/2157-7412.1000103.
Colombian Office Action received Jul. 19, 2022, in connection with corresponding CO Application No. NC2020/0000260 (12 pp., including machine-generated English translation).
Japanese Office Action received Jul. 26, 2022, in connection with corresponding JP Application No. 2021-523841 (10 pp., including machine-generated English translation).
Wall, J.S., et al. "Radioimaging of Light Chain Amyloid with a Fibril-Reactive Monoclonal Antibody", The Journal of Nuclear Medicine, vol. 47, No. 12, Nov. 30, 2006 (Nov. 30, 2006), pp. 2016-2024, XP055970051.
Wall, J.S., et al. "Development and evaluation of agents for targeting visceral amyloid", Tijdschrift Voor Nu[C] Leaire Geneeskunde, vol. 33, No. 4. Dec. 1, 2011 (201-12-01), p. 807, XP055574438, Netherlands ISSN: 1381-4842.
Supplementary European Search Report received Apr. 6, 2023 for corresponding EP Application No. 198807380.
Koyama, Jun , et al. "History of Medicine", 2015, vol. 252, No. 10, p. 1087-1092.
Japanese Office Action dated Oct. 24, 2023 and its English translation, of corresponding JP Application No. 2020-505320.

* cited by examiner

Figure 2

```
         10                  30                  50
caggtgcagctgaaggagtcaggacctggcctggtggcgccctcacagagcctgtccatc
----------+---------+---------+---------+---------+---------+
gtccacgtcgacttcctcagtcctggaccggaccaccgcgggagtgtctcggacaggtag
 Q  V  Q  L  K  E  S  G  P  G  L  V  A  P  S  Q  S  L  S  I 70                  90                 110
                                    ------CDR1------
acatgcactgtctcagggttctcattaagcagctatggtgtaagctgggttcgccagcct
----------+---------+---------+---------+---------+---------+
tgtacgtgacagagtcccaagagtaattcgtcgataccacattcgacccaagcggtcgga
  T  C  T  V  S  G  F  S  L  S  S  Y  G  V  S  W  V  R  Q  P 130                 150                 170
                                     -----------------------
ccaggaaagggtctggagtggctgggagtaatatgggggtgacgggagcacaaattatcat
----------+---------+---------+---------+---------+---------+
ggtcctttcccagacctcaccgaccctcattataccccactgccctcgtgtttaatagta
  P  G  K  G  L  E  W  L  G  V  I  W  G  D  G  S  T  N  Y  H 190                 210                 230
------CDR2----------------------
ccaaatctcatgtccagactgagtatcagcaaggatatttccaagagccaagttctcttc
----------+---------+---------+---------+---------+---------+
ggtttagagtacaggtctgactcatagtcgttcctataaaggttctcggttcaagagaag
  P  N  L  M  S  R  L  S  I  S  K  D  I  S  K  S  Q  V  L  F 250                 270                 290
                                                    --CDR3---
aaactgaatagtctgcaaactgatgacacagccacgtactactgtgtcaccttggactac
----------+---------+---------+---------+---------+---------+
tttgacttatcagacgtttgactactgtgtcggtgcatgatgacacagtggaacctgatg
  K  L  N  S  L  Q  T  D  D  T  A  T  Y  Y  C  V  T  L  D  Y 310                 330
tggggtcaaggaacctcagtcaccgtctcctca
----------+---------+---------+----
accccagttccttggagtcagtggcagaggagt
  W  G  Q  G  T  S  V  T  V  S  S
```

Figure 3

```
            10                  30                  50
gatgttgtgatgacccaaactccactctacctgcctgtcagtcttggagatcaagcctac
------------+---------+---------+---------+---------+---------+
ctacaacactactgggtttgaggtgagagggacggacagtcagaacctctagttcggagg
 D  V  V  M  T  Q  T  P  L  S  L  P  V  S  L  G  D  Q  A  S 70                  90                 110
                                 ---------CDR1---------------
atctcttgcagatctagtcagagccttgtacatagaaatggaaacacctatttacattgg
------------+---------+---------+---------+---------+---------+
tagagaacgtctagatcagtctcggaacatgtatctttaccttt gtggataaatgtaacc
 I  S  C  R  S  S  Q  S  L  V  H  R  N  G  N  T  Y  L  H  W 130                 150                 170
                                                    -----CDR2---
tacctgcagaagccaggccagtctccaaagctcctgatctacaaagtttccaaccgattt
------------+---------+---------+---------+---------+---------+
atggacgtcttcggtccggtcagaggtttcgaggactagatgtttcaaaggttggctaaa
 Y  L  Q  K  P  G  Q  S  P  K  L  L  I  Y  K  V  S  N  R  F 190                 210                 230
tctggggtcccagacaggttcagtggcagtggatcagggacagatttcacactcaagatc
------------+---------+---------+---------+---------+---------+
agacccc agggtctgtccaagtcaccgtcacctagtccctgtctaaagtgtgagttctag
 S  G  V  P  D  R  F  S  G  S  G  S  G  T  D  F  T  L  K  I 250                 270                 290
                                                     --------CDR3---
agcagagtggaggctgaggatttggggactttatttctgttttcaaactacatatgttccg
------------+---------+---------+---------+---------+---------+
tcgtctcacctccgactcctaaaccctgaaataaagacaaaagtttgatgtatacaaggc
 S  R  V  E  A  E  D  L  G  L  Y  F  C  F  Q  T  T  Y  V  P 310                 330
aacacgttcggaggggggaccaagctggaaataaaa
------+---------+---------+---------+
ttgtgcaagcctccccctggttcgacctttatttt
 N  T  F  G  G  G  T  K  L  E  I  K
```

Figure 6

```
5'-aagcttgccgccaccatgaagttgcctgttaggctgttggtgc-3'

HindIII  Kozak                    Leader
aagcttgccgccaccatgaagttgcctgttaggctgttggtgctgatgttctggattcctgcttccagcagt
------+---------+---------+---------+---------+---------+---------+
ttcgaacggcggtggtacttcaacggacaatccgacaaccacgactacaagacctaaggacgaaggtcgtca
          M  K  L  P  V  R  L  L  V  L  M  F  W  I  P  A  S  S  S 10           30           60
gatgttgtgatgacccaaactccactctccctgcctgtcagtcttggagatcaagcctcc
------+---------+---------+---------+---------+---------+
ctacaacactactgggtttgaggtgagagggacggacagtcagaacctctagttcggagg
  D  V  V  M  T  Q  T  P  L  S  L  P  V  S  L  G  D  Q  A  S 70           90          110
                              ----------------CDR1-----------------
atctcttgcagatctagtcagagccttgtacatagaaatggaaacacctatttacattgg
------+---------+---------+---------+---------+---------+
tagagaacgtctagatcagtctcggaacatgtatctttacctttgtggataaatgtaacc
  I  S  C  R  S  S  Q  S  L  V  H  R  N  G  N  T  Y  L  H  W 130          150          170
                                          -----------CDR2---
tacctgcagaagccaggccagtctccaaagctcctgatctacaaagtttccaaccgattt
------+---------+---------+---------+---------+---------+
atggacgtcttcggtccggtcagaggttcgaggactagatgtttcaaaggttggctaaa
  Y  L  Q  K  P  G  Q  S  P  K  L  L  I  Y  K  V  S  N  R  F 190          210          230
tctggggtcccagacaggttcagtggcagtggatcagggacagatttcacactcaagatc
------+---------+---------+---------+---------+---------+
agaccccagggtctgtccaagtcaccgtcacctagtccctgtctaaagtgtgagttctag
  S  G  V  P  D  R  F  S  G  S  G  S  G  T  D  F  T  L  K  I 250          270          290
                                     ---------------CDR3---
agcagagtggaggctgaggatttgggactttatttctgttttcaaactacatatgttcag
------+---------+---------+---------+---------+---------+
tcgtctcacctccgactcctaaacccctgaaataaagacaaaagtttgatgtatacaagtc
  S  R  V  E  A  E  D  L  G  L  Y  F  C  F  Q  T  T  Y  V  P 310          330
------                                         BamHI
aacacgttcggaggggggaccaagctggaaatcaaacgtgagtggatcc
------+---------+---------+---------+---------+
ttgtgcaagcctccccctggttcgaccttagtttgcactcacctagg
  N  T  F  G  G  G  T  K  L  E  I  K 3'-agcctccccctggttcgacctttagtttgcactcacctagg-5'
```

Figure 7

5'-aagctttccgccaccatggctgtcctggggctgctcttctgc-3'

HindIII Kozak                         Leader
aagcttgccgccaccatggctgtcctggggctgctcttctgcctggtgacattcccaagctgtgtcctgtcc
ttcgaacggcggtggtaccgacaggaccccgacgagaagacggaccactgtaagggttcgacacaggacagg
        M  A  V  L  G  L  L  F  C  L  V  T  F  P  S  C  V  L  S 10              30              50 caggtgcagctgaaggagtcaggacctggcctggtggcgccctcacagagcctgtccatc
gtccacgtcgacttcctcagtcctggaccggaccaccgcgggagtgtctcggacaggtag
 Q  V  Q  L  K  E  S  G  P  G  L  V  A  P  S  Q  S  L  S  I 70              90              110
                                        ------CDR1------
acatgcactgtctcagggttctcattaagcagctatggtgtaagctgggttcgccagcct
tgtacgtgacagagtcccaagagtaattcgtcgatacgacattcgacccaagcggtcgga
 T  C  T  V  S  G  F  S  L  S  S  Y  G  V  S  W  V  R  Q  P 130             150             170
                                                -----
ccaggaaagggtctggagtggctggggtaatatggggtgacggagcacaaattatcat
ggtcctttcccagacctcaccgaccctcattataccccactgcctcgtgtttaatagta
 P  G  K  G  L  E  W  L  G  V  I  W  G  D  G  S  T  N  Y  H 190             210             230
------CDR2------
ccaaatctcatgtccagactgagtatcagcaaggatatttccaagagacaagttctcttc
ggtttagagtacaggtctgactcatagtcgttcctataaaggttctcggttcaagagaag
 P  N  L  M  S  R  L  S  I  S  K  D  I  S  K  S  Q  V  L  F 250             270             290
                                                --CDR3---
aaactgaatagtctgcaaactgatgacacagccacgtactactgtgtcaccttggactac
tttgacttatcagacgtttgactactgtgtcggtgcatgatgacacagtggaacctgatg
 K  L  N  S  L  Q  T  D  D  T  A  T  Y  Y  C  V  T  L  D  Y 310             330
                                   ----------CH1---------->
tggggtcaaggaacctcagtcaccgtctcctcagcctccaccaagggcccatcgg
accccagttccttggagtcagtggcagaggagtcggaggtggttcccgggtagcc
 W  G  Q  G  T  S  V  T  V  S  S
                                           ApaI 3'-ccttggagtcagtggcagaggagtcggaggtggttcccgggtagcc-5'

METHODS AND COMPOSITIONS FOR IMAGING AMYLOID DEPOSITS

CLAIM FOR PRIORITY

This application claims priority from U.S. provisional application 62/753,410, filed Oct. 31, 2018, which is incorporated herein in its entirety.

CROSS-REFERENCE TO RELATED APPLICATION

This application is a continuation-in-part of U.S. application Ser. No. 16/021,168, filed Jun. 28, 2018, and claims the benefit thereof.

REFERENCE TO A SEQUENCE LISTING SUBMITTED BY EFS-WEB

The contents of the ASCII text file of the sequence listing named "8441-0018-1-ST25", which is 16.9 kb in size, was created on Jan. 22, 2019, and was electronically submitted via EFS-WEB with this application, is incorporated herein by reference in its entirety.

FIELD OF THE INVENTION

The present disclosure relates to humanized and chimeric (e.g., mouse-human) antibodies and antigen-binding fragments thereof having a detectable molecule linked or conjugated thereto and to methods of using the same to detect and image amyloid deposits.

BACKGROUND OF THE INVENTION

The following discussion is provided merely to aid the reader in understanding the disclosure and is not admitted to describe or constitute prior art thereto.

Native antibodies are usually heterotetrameric glycoproteins of about 150,000 daltons composed of two identical light chains and two identical heavy chains. Each light chain is linked to a heavy chain by one disulfide bond, while the number of additional disulfide linkages between the heavy chains varies with different antibody isotypes. The simplest isotype is IgG, which comprises just two light chains and two heavy chains, in which the two heavy chains are linked by two disulfide linkages. Each heavy chain has a variable domain ($V_H$) at one end with a number of adjacent constant domains. Each light chain has a variable domain ($V_L$) at one end and a constant domain at its other end. Each variable domain of the light and heavy chain in an antibody comprises three segments called complementarity-determining regions ("CDR") or hypervariable regions. Each CDR in a light chain, together with the corresponding CDR in the adjacent heavy chain, form an antigen-binding site of the antibody. Light chains are of two major types, K and A, depending on their constant region. Both K and A light chains may combine with any of the different heavy chain types.

Amyloid light-chain amyloidosis (AL amyloidosis, AL, or ALA), also called primary amyloidosis, is the most common form of systemic amyloidosis in the United States. The term "amyloidosis" refers to a cluster of diseases which share a common feature, i.e., the extracellular deposition of pathologic insoluble fibrillar proteins in organs and tissues (Rodney, et al.—*NEJM*, 25:898). Amyloidosis is caused by malfunction of a person's antibody-producing cells causing production of abnormal protein fibers which aggregate to form insoluble amyloid deposits in organs and tissues. The type of amyloidosis is determined by the nature of the precursor proteins which form the fibril deposit. In primary amyloidosis, the fibrils comprise fragments of immunoglobulin light chains and in secondary amyloidosis, the fibrils comprise amyloid A protein. Modern classification of amyloidosis is based on the nature of the precursor plasma proteins which form the fibril deposit.

The precursor plasma proteins are diverse and unrelated. Nevertheless, all precursor deposits produce amyloid deposits that share a common typical β-pleated-sheet configuration, which is responsible for the typical staining properties of the fibrillar deposits. The final stage in the development of amyloidosis is the deposit of amyloid fibrils in the organs of the sufferer. Amyloidosis mortality is high, with current five-year survival rates of about 28%.

To date, the treatment of AL has been directed towards reducing the synthesis of amyloidogenic precursor light chains by attacking the malfunctioning cells through conventional or high dose cytotoxic chemotherapy. Despite the improved prognosis gained by eliminating the offending plasma cell clone, mortality remains high due to multi-organ dysfunction caused by persistent, insoluble amyloid fibril deposits. This treatment suffers from two disadvantages. First, the fibrillar amyloid deposits are often asymptomatic until after significant deposition has taken place. Therefore, treatment is unlikely to be undertaken before significant deposits have already occurred. Second, since this treatment is, at best, effective only to stop the production of precursor abnormal protein but not to remove the existing deposits, prognosis for AL patients remains exceedingly poor due to persistence (or progression) of the pathologic deposits (Solomon, et al.—*Int. J. Exp. Clin. Invest.* 2:269).

As a result, therapeutic targeting and clearance of amyloid deposits is an area of intense medical interest. Ancillary to this is intense interest in detecting the presence and location of amyloid deposits and monitoring the clearance of amyloid deposits as an adjunct to the aforementioned targeting and clearance. The compositions and methods disclosed herein fulfill this need for detecting such presence and location.

SUMMARY OF THE INVENTION

Described herein are compositions and methods for detecting the presence, location, and amount of amyloid deposits, including those resulting from primary (AL) amyloidosis. The disclosed compositions comprise a humanized or chimeric antibody or fragment thereof ("antigen-binding fragment") that specifically binds to amyloid deposits (e.g., amyloid light chain fibrils) and to which is linked a detectable molecule. The disclosed method comprises administering to a subject suspected of having amyloid deposits the above-described composition and detecting the presence, quantity, and/or location of the amyloid deposits by detection of the detectable molecule by diagnostic imaging.

The present methods also include a method of stratifying patients for therapy with the disclosed humanized or chimeric antibody based on the affinity of the diagnostic composition for the amyloid deposits. The present methods also include determining the appropriate dosage of the disclosed humanized or chimeric antibody for therapy based on the affinity of the diagnostic compositions for the amyloid deposits. That is, one may determine the appropriate dosing of a patient based on the detected affinity (uptake) of the labeled antibody or antibody fragment. A patient showing strong affinity for the labeled antibody or antigen-binding antibody fragment may require a smaller amount of therapeutic antibody or antigen-binding antibody fragment than a patient showing a weaker affinity for the labeled antibody or antigen-binding antibody fragment. The present disclosure therefore provides a method of determining the appropriate dosage of the disclosed humanized or chimeric antibody for therapy comprising the steps of administering to the patient a labeled antibody or antibody fragment disclosed herein, determining the affinity of the labeled antibody or antibody fragment for the amyloid deposits, and administering a dose or series of doses of chimeric or humanized antibody or antibody fragment based on the strength of the affinity.

In some embodiments, the disclosed antibody in the diagnostic compositions comprises a $V_K$ region comprising SEQ ID NO: 47 and a $V_H$ region comprising SEQ ID NO: 48. In some embodiments, the antibody comprises a constant region derived from a human IgG1. In some embodiments, the antibody binds to amyloid fibrils with a higher affinity than its murine equivalent. In some embodiments, the antibody binds to an epitope expressed by the β-pleated sheet configuration of amyloid fibrils with higher affinity than a mouse antibody comprising a $V_K$ region of SEQ ID NO: 36 and a $V_H$ region of SEQ ID NO: 35. And in some embodiments, the antibody binds to kappa and lambda amyloid fibrils in vivo.

In another aspect, the present disclosure provides compositions comprising the disclosed humanized or chimeric antibody linked to a detectable label or molecule and a pharmaceutically acceptable carrier.

A chimeric antibody useful in the subject methods and compositions may be produced by co-transfection in mammalian cells of the vector constructs 11-1F4VK.pKN100 and 11-F4VH.pG1D200 or transfection in mammalian cells of the supervector construct pG1KD200-11-1F4. In some embodiments, the co-transfection of the vector constructs 11-1F4VK.pKN100 and 11-F4VH.pG1D200 or transfection of a supervector construct pG1KD200-11-1F4 takes place in COS cells. The antibody thus produced is designated "chimeric 11-1F4 antibody". As disclosed elsewhere herein, fragments of the chimeric 11-1F4 antibody are also useful in the subject methods and compositions.

In some embodiments, the amyloid deposits detected result from primary amyloidosis. In some embodiments, the primary amyloidosis comprises involvement of at least one organ or tissue selected from the group consisting of heart, kidneys, liver, lung, gastrointestinal tract, nervous system, muscular skeletal system, soft tissue, and skin and the deposits are detected in one or more of those organs.

In one aspect, the present disclosure provides methods of detecting or imaging amyloid deposits comprising administering to a patient diagnosed with or suspected of having an amyloid deposition disease a diagnostically effective amount of a humanized or chimeric antibody or an antigen-binding fragment thereof having a detectable label or marker linked thereto and detecting the presence, location, and/or quantity of the detectable label bound to amyloid deposits in the patient's body by diagnostic imaging. In this aspect, the antibody or antigen-binding fragment may comprise: a variable heavy chain ($V_H$) comprising: a complementarity determining region (CDR) H1 comprising SEQ ID NO: 52; a CDRH2 comprising SEQ ID NO: 53; and a CDRH3 comprising SEQ ID NO: 54; and a variable light chain ($V_K$) comprising a CDRL1 comprising SEQ ID NO: 49; a CDRL2 comprising SEQ ID NO: 50; and a CDRL3 comprising SEQ ID NO: 51. In another aspect, the present disclosure provides compositions of the aforementioned antibody or antibody fragment linked to a detectable molecule and a pharmaceutically-acceptable carrier.

In some embodiments of the foregoing aspects, the antibody or antigen-binding fragment thereof may be a humanized antibody, while in some embodiments, the antibody or antigen-binding fragment thereof may be a chimeric antibody.

In some embodiments of the foregoing aspects, the $V_K$ region of the antibody or antigen-binding fragment may comprise SEQ ID NO: 47 and the $V_H$ region may comprise SEQ ID NO: 48.

In some embodiments of the foregoing aspects, the antibody or antigen-binding fragment may comprise a constant region that is derived from a human IgG1. In some embodiments, the antibody may be chimeric 11-1F4 antibody.

In another aspect, the present disclosure provides methods of detection of an amyloid deposition disease in a patient suspected of having such disease by administering a labeled antibody or an antigen-binding fragment thereof and detecting the presence of the label in the patient by diagnostic imaging.

In some embodiments of this aspect, the humanized or chimeric 11-1F4 antibody comprises a constant region is derived from a human IgG1.

In another embodiment, the present disclosure provides an in vivo method of detecting the presence, location, and/or amount of amyloid deposits in a patient suspected of having amyloid deposits which comprises administering to the patient an antibody or antigen binding fragment having a detectable molecule linked thereto, the antibody or antigen-binding fragment comprising: a variable heavy chain ($V_H$) comprising: a complementarity determining region (CDR) H1 comprising SEQ ID NO: 53; a CDRH2 comprising SEQ ID NO: 53; and a CDRH3 comprising SEQ ID NO: 54; and a variable light chain ($V_K$) comprising a CDRL1 comprising SEQ ID NO: 49; a CDRL2 comprising SEQ ID NO: 50; and a CDRL3 comprising SEQ ID NO: 51; and detecting the presence, location, and/or quantity of amyloid deposits by detection of the detectable label bound to the amyloid deposits by diagnostic imaging.

In another embodiment, the disclosure provides an in vivo method of detecting the presence, location, and/or quantity of amyloid deposits in a patient suspected of having amyloid deposits which comprises administering to the patient an antibody or antigen binding fragment having a detectable molecule linked thereto, the antibody or antigen-binding fragment comprising: a $V_K$ region comprising SEQ ID NO: 47 and a $V_H$ region comprising SEQ ID NO: 48; and detecting the presence, location, and/or quantity of amyloid deposits bound to the amyloid deposits by detection of the detectable label by diagnostic imaging.

In one aspect of either of the above methods, the disclosure provides the above-described methods wherein the method of detection is positron emission spectroscopy (PET). In the aspects wherein the method of detection is PET, the detectable label may be $^{124}$I or $^{89}$Zr. In another aspect of the above methods, the antibody is selected from a chimeric or humanized 11-1F4, antigen-binding fragments thereof, and the antibody CAEL-101. In still another aspect of the above methods, the amyloid deposits are in the heart.

In another embodiment, the present disclosure provides a composition for detecting the presence of amyloid deposits in a subject which comprises an antibody or antigen binding fragment having a detectable molecule linked thereto, the antibody or antigen-binding fragment comprising: a variable heavy chain ($V_H$) comprising: a complementarity determining region (CDR) H1 comprising SEQ ID NO: 53; a CDRH2 comprising SEQ ID NO: 53; and a CDRH3 comprising SEQ ID NO: 54; and a variable light chain ($V_K$) comprising a CDRL1 comprising SEQ ID NO: 49; a CDRL2 comprising SEQ ID NO: 50; and a CDRL3 comprising SEQ ID NO: 51.

In another embodiment, the present disclosure provides a composition for detecting the presence of amyloid deposits in a subject which comprises an antibody or antigen binding fragment having a detectable molecule linked thereto, the antibody or antigen-binding fragment comprising: a $V_K$ region comprising SEQ ID NO: 47 and a $V_H$ region comprising SEQ ID NO: 48.

In one aspect of the above compositions, the detectable molecule is selected from $^{124}I$ and $^{89}Zr$. In another aspect of the above compositions, the antibody is selected from chimeric or humanized 11-1F4 or antigen-binding fragments thereof and the antibody CAEL-101. In yet another aspect of the above compositions, the amyloid deposits are in the heart.

In another embodiment, the present disclosure provides a method of monitoring disease progression in a patient diagnosed with an amyloid deposition disease and having amyloid deposits comprising the steps of: a) administering to said patient a composition described in the previous paragraphs and conducting diagnostic imaging on the patient to detect the amount of detectable molecule bound to the amyloid deposits, b) treating the patient with a therapy intended to remove amyloid deposits, c) administering to said patient a composition described in the previous paragraphs, d) conducting diagnostic imaging on the patient to detect the amount of detectable molecule bound to the amyloid deposits, and e) comparing the detected amount of detectable molecule in step d to the detected amount of detectable molecule in step a.

In the above method, the patient may be treated in step b) with an antibody selected from a humanized or chimeric 11-1F4 antibody or antigen-binding fragment thereof and the antibody CAEL-101. In the above method, the composition may be any of the compositions described above. In another aspect, the method of detection may be PET. In another aspect, if the detection method is PET, the detectable label is selected from $^{124}I$ and $^{89}Zr$. In another aspect of the above methods, the antibody is selected from humanized or chimeric 11-1F4 or antigen-binding fragments thereof and CAEL-101. In another aspect of the above methods, the amyloid deposits are in the heart.

In another embodiment, the present disclosure provides a method of determining the effectiveness of treatment to remove amyloid deposits in a patient comprising a) treating the patient with a therapeutically-effective dose of the humanized or chimeric 11-F4 antibody or antibody fragment thereof, b) administering to the patient a diagnostically-effective amount of one of the above-described compositions, and c) measuring by diagnostic imaging the amount of detectable molecule from the diagnostic composition in the lymph nodes of the patient, wherein the higher the amount of detectable molecule detected in the lymph nodes, the more effective the treatment. In one aspect of this embodiment, the amyloid deposits are in the heart.

In some embodiments of this disclosure, the chimeric 11-1F4 antibody is CAEL-101, the antibody produced by the CHO cells deposited with the ATCC as ACC No. PTA-125146.

In some embodiments, the primary amyloidosis consists of lambda light chain fibril aggregate deposits, while in some embodiments, the primary amyloidosis consists of kappa light chain fibril aggregate deposits, and in still other embodiments, the primary amyloidosis consists of kappa and lambda light chain fibril aggregate deposits.

The foregoing general description and following detailed description are exemplary and explanatory and are intended to provide further explanation of the invention.

BRIEF DESCRIPTION OF THE DRAWINGS

FIG. 2 is a listing of DNA and amino acid sequences of the murine 11-1F4 antibody $V_H$ region gene, SEQ ID NO: 39 and NO: 35, respectively.

FIG. 3 is a listing of DNA and amino acid sequences of the murine 11-1F4 antibody $V_K$ region gene, SEQ ID NO: 40 and NO: 36, respectively.

FIG. 6 is a listing of the DNA and amino acid sequences of the modified murine 11-1F4 antibody $V_K$ region gene (SEQ ID NO: 42 and NO: 47, respectively) and the sequences of the oligonucleotide primers used to modify the $V_K$ gene (SEQ ID NO: 41 and NO: 43, respectively).

FIG. 7 is a listing of the DNA and amino acid sequences of the modified murine 11-1F4 antibody $V_H$ region gene (SEQ ID NO: 45 and NO: 48, respectively) and the sequences of the oligonucleotide primers used to modify the VH gene (SEQ ID NO: 44 and NO: 46, respectively).

DETAILED DESCRIPTION OF THE INVENTION

Figure 1:
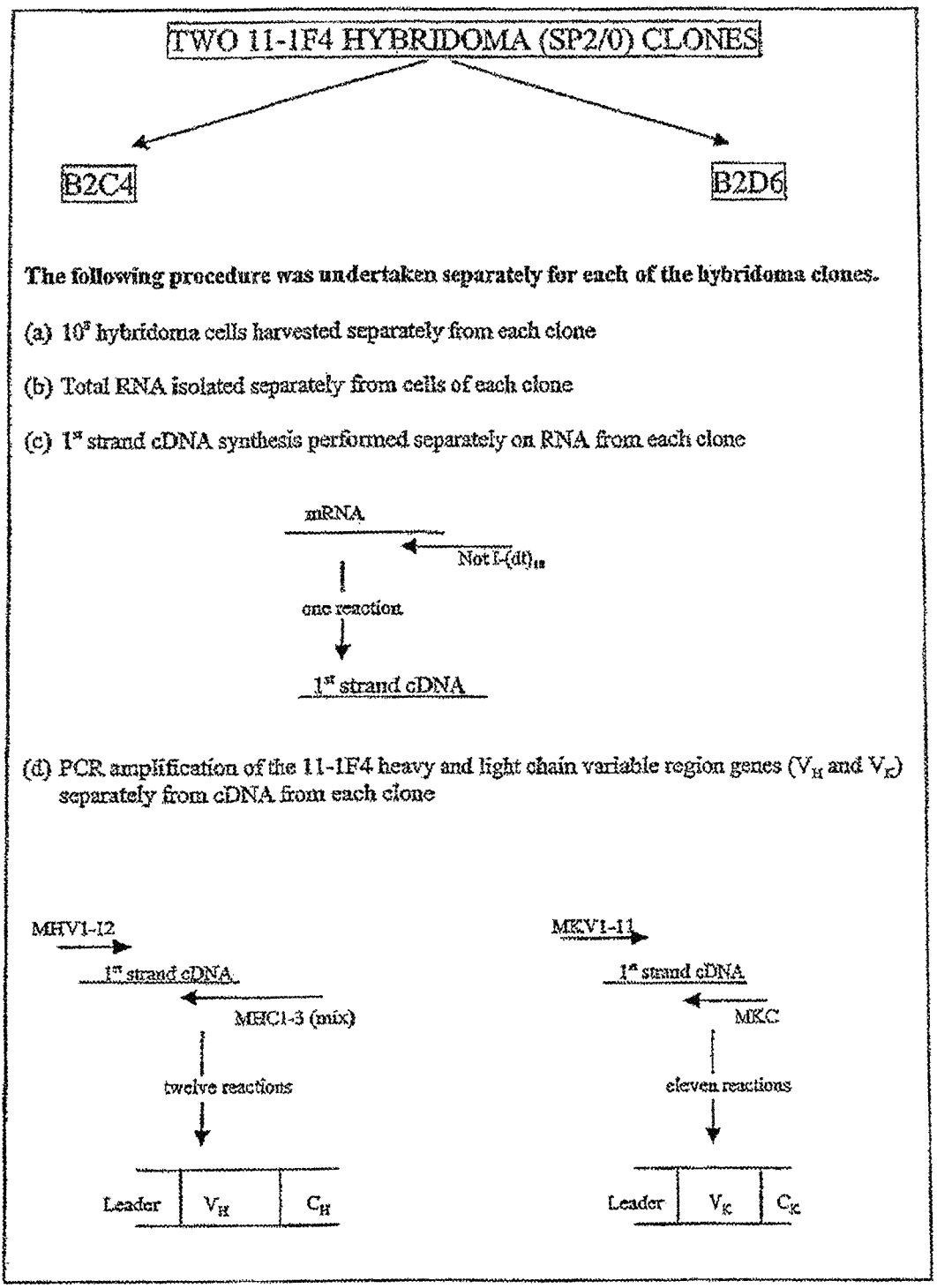
FIG. 1 outlines the strategy used to clone the murine $V_H$ and $V_K$ genes from a hybridoma cell line.

In accordance with the present disclosure, compositions comprising humanized antibodies, chimeric antibodies (e.g., mouse-human antibodies) or antigen-binding fragments thereof to which in each case is linked a detectable molecule are provided that are useful for detecting the presence, location, and amount of amyloid deposits in vivo. These compositions allow detection, localization, and/or quantification of amyloid deposits while producing little or no human anti-mouse antibody (HAMA) reaction. The disclosure provides compositions comprising at least one of said antibodies or antibody fragments linked to a detectable marker and a pharmaceutically acceptable carrier and methods of detecting the location and amount of amyloid deposits by administering to a patent an amount of said marker-linked antibody or antibody fragment effective to allow detection of amyloid deposits if such deposits are present and detecting the presence, amount, and/or location of the detectable marker bound to the amyloid deposits by diagnostic imaging.

Further in accordance with the present disclosure, methods are provided for monitoring or determining the effect of treating amyloid deposition diseases. The method of monitoring disease progression in a patient diagnosed with an amyloid deposition disease and having amyloid deposits comprises the steps of:
a. administering to said patient a diagnostically effective amount of a humanized or chimeric 11-1F4 antibody or an antigen-binding fragment thereof having a detectable molecule linked thereto and detecting the amount of detectable molecule bound to the amyloid deposits,
b. treating the patient with therapy intended to remove amyloid deposits, such as a humanized or chimeric 11-1F4 antibody or antigen-binding fragment thereof,
c. administering to said patient a diagnostically effective amount of a humanized or chimeric 11-1F4 antibody or an antigen-binding fragment thereof having a detectable molecule linked thereto and detecting the amount of detectable molecule bound to the amyloid deposits, and
d. comparing the detected amount of detectable molecule in step c to the detected amount of detectable molecule in step a.

In this embodiment, the present disclosure is directed towards measuring the extent of change in the amount of amyloid deposits of a patient (if any) by administering to said patient the marker-linked antibody or antibody fragment as described herein both prior to and after a treatment intended to remove amyloid deposits and measuring the difference in the size and extent of the detected amyloid deposits after the treatment compared to the size and extent measured prior to the treatment.

Further provided is an in vivo method of detecting amyloid deposits in a subject, the method comprising: a) administering to the subject a composition comprising one or more than one antibody or antigen-binding fragment thereof as described herein linked to a detectable molecule; and b) detecting by diagnostic imaging the detectable agent linked to the antibody or antigen-binding fragment thereof bound to the amyloid deposits.

In the method described above, the step of detecting (step b) may be performed using PET (positron emission tomography), SPECT (single-photon emission computed tomography), MRI, fluorescence imaging, or any other suitable diagnostic imaging method. PET is the preferred imaging method. The use of PET for imaging tumors or other deposits using a detectable molecule is well known. This preparation of diagnostic imaging agents and their use in PET are described, for example, in Bailly, et al.—*Int. J. Mol. Sci.* 2017, 18, 57; Boerman, et al.—*J Nucl Med,* 2011; 52:1171-1172; and Mayer, et al.—*J Nucl Med* 2017; 58:538-546, all of which are incorporated herein by reference in their entirety. Although these references are directed mainly at cancerous tumor detection, the materials and methods disclosed therein are equally useful for detecting amyloid deposits.

The in vivo imaging step in the methods described above may be whole body imaging for diagnostic purposes or local imaging at specific sites, such as but not limited to heart, kidney, liver, spleen, nervous system, or digestive system in a quantitative manner to assess the progression of disease or patient response to a treatment regimen. The detection step in the methods as described above may be any diagnostic imaging technology including, but not limited to: positron emission tomography (PET), wherein the detectable agent is an isotope such as $^{11}$C, $^{13}$N, $^{15}$O, $^{18}$F, $^{64}$Cu, $^{62}$Cu, $^{124}$I, $^{76}$Br, $^{82}$Rb, $^{89}$Zr, or $^{68}$Ga; single photon emission computed tomography (SPECT), wherein the detectable agent is a radiotracer such as $^{99m}$Tc, $^{111}$In, $^{123}$I, $^{201}$Tl, or $^{133}$Xe, depending on the specific application; magnetic resonance imaging (MRI), wherein the detectable agent may be, for example and not limited to, gadolinium, iron oxide nanoparticles and carbon-coated iron-cobalt nanoparticles. In illustrative examples herein, antibodies are labeled with $^{124}$I or $^{89}$Zr.

The detectable molecule (sometimes described herein as a "label", "marker", or "agent") as described herein may be linked, also sometimes referred to herein as "conjugated", to the antibody or fragment thereof by any suitable method known in the art. For example, and without wishing to be limiting, the detectable agent may be linked to the antibody or antibody fragment by a covalent bond or ionic interaction. The linkage may be achieved through a chemical cross-linking reaction, or through fusion using recombinant DNA methodology combined with any peptide expression system, such as bacteria, yeast or mammalian cell-based systems. Methods for linking an antibody or fragment thereof to a detectable agent are well-known to a person of skill in the art, as shown in the references cited above.

Further provided herein is a method of determining the appropriate dosage of the disclosed humanized or chimeric antibody for therapy based on the affinity of the diagnostic compositions for the amyloid deposits as determined by the uptake of the diagnostic composition by the amyloid deposits of the patient. That is, one may determine the dosing of a patient based on the detected uptake of the labeled antibody or antibody fragment. A patient showing higher uptake of the labeled antibody or antibody fragment may require a smaller amount of therapeutic antibody or antibody fragment than a patient showing a lower uptake of the labeled antibody or antibody fragment. The present disclosure therefore provides a method of determining the appropriate dosage of the disclosed humanized or chimeric antibody for therapy comprising the steps of administering to the patient a labeled antibody or antibody fragment disclosed herein, determining the uptake of the labeled antibody or antibody fragment by the amyloid deposits, and administering a dose or series of doses of chimeric or humanized antibody or antibody fragment based on the detected amount of uptake.

Further provided herein is a method of determining the effectiveness of a treatment with the chimeric or humanized antibody or antibody fragment disclosed herein to remove amyloid deposits. The method comprises: a) treating the patient with a therapeutically-effective dose of a therapy intended to remove amyloid deposits, such as the chimeric or humanized antibody or antibody fragment disclosed herein, b) administering to the patient a diagnostically-effective amount of the diagnostic composition disclosed herein, and c) measuring the amount of detectable molecule from the diagnostic composition in the lymph nodes of the patient, wherein the higher the amount of detectable molecule detected in the lymph nodes, the more effective the treatment.

Definitions

It is to be understood that methods are not limited to the particular embodiments described, and as such may vary. It is also to be understood that the terminology used herein is for the purpose of describing particular embodiments only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "about" means plus or minus 10%.

As used herein, "optional" or "optionally" means that the subsequently described event or circumstance may or may not occur, and that the description includes instances where said event or circumstance occurs and instances where it does not.

As used herein, the terms "individual", "patient", or "subject" can be an individual organism, a vertebrate, a mammal (e.g., a bovine, a canine, a feline, or an equine), or a human. In a preferred embodiment, the individual, patient, or subject is a human.

As used herein, the term an "isolated antibody" is intended to refer to an antibody which is substantially free of other antibodies having different antigenic specificities (e.g., an isolated antibody that specifically binds to an amyloid fibril is substantially free of antibodies that do not bind to amyloid fibrils). An isolated antibody that specifically binds to an epitope of an amyloid light chain fibril (e.g., a kappa and/or lambda fibril) may, however, have crossreactivity to other proteins, such as amyloid A fibrils. However, the antibody preferably always binds to human amyloid light chain fibrils. In addition, an isolated antibody is typically substantially free of other cellular material and/or chemicals.

As used herein, the phrase "diagnostically effective amount" means the amount of detectable marker-linked antibody or antibody fragment which, when administered to a patient or subject, permits in vivo detection, localization, and/or quantification by diagnostic imaging of amyloid deposits in the patient or subject if any such deposits are present. It is emphasized that a diagnostically effective amount will not always be effective to detect amyloid deposits, even though such amount is deemed to be a diagnostically effective amount by those of skill in the art. The diagnostically effective amount may vary based on the route of administration and dosage form, the age and weight of the subject, and/or the subject's condition, including the type and stage of the amyloidosis at the time that diagnosis commences, among other factors.

As used herein, the term "humanized antibody" refers to an antibody that comprises the CDRs of antibodies derived from mammals other than human, and the framework region (FR) and the constant region of a human antibody. A humanized antibody is useful as a component in a diagnostic composition according to the present disclosure since antigenicity of the humanized antibody in human body is lowered.

As used herein, the term "antibody fragment" refers to a part of an antibody that comprises a CDR of the antibody but has been engineered to delete some of the structure of the intact antibody. Engineering antibody fragments is well known in the art, as shown (for example) in Holliger, et al.—*Nature Biotechnology:* 23 (9), 1126-1135 (2005), incorporated herein by reference in its entirety. The term "antigen-binding fragment" as used herein means an antibody fragment that binds to amyloid deposits.

As used herein, the term "pharmaceutically-acceptable carrier" means a material for admixture with a pharmaceutical or diagnostic compound (e.g., a chimeric antibody linked to a detectable molecule) for administration to a patient as described, for example, in "Ansel's Pharmaceutical Dosage Forms and Delivery Systems", Tenth Edition (2014).

As used herein, the synonymous terms "detectable molecule", "detectable marker", "detectable agent", and "detectable label" refer to substances that may be detected in vivo by diagnostic imaging techniques, such as (but not limited to) PET, SPECT, and MRI.

As used herein, the terms "diagnostic imaging" or "imaging" mean methods of in vivo imaging of a detectable molecule in a patient or subject to determine the presence, location and/or amount of a tissue or substance (such as an amyloid deposit) in the patient or subject to which the detectable molecule has been localized, such as by being linked to an antibody or antibody fragment that binds to the tissue or substance to be detected.

Anti-AL Antibodies

Murine Anti-Fibril Antibodies

Recent animal studies have shown that the administration of the murine 11-1F4 antibody and other murine anti-human light chain specific antibodies directed against an epitope common to the R-pleated-sheet structure present on AL fibrils results in complete degradation of the human ALK and ALA amyloid deposits. Some of these murine antibodies are described in U.S. Pat. No. 8,105,594 ("the '594 patent"), which is incorporated herein by reference in its entirety.

Murine antibodies are generally unsuitable for administration to other animal species (such humans) because the receiving species will recognize the murine antibody as antigenic and will produce antibodies against it. The antigenicity of an antibody from one species when injected into another species is normally caused by a portion of a constant domain. Such an antigenic response will impede or prevent the desired therapeutic or diagnostic effect of the murine antibody. In humans, this antigenic response is called human anti-mouse antibody (HAMA). The antibodies described in the '594 patent have the potential to be highly immunogenic in humans via the human anti-mouse antibody (HAMA) response. Since the HAMA response usually results in the rapid clearance of a mouse antibody from the human recipient, HAMA would severely limit any potential human therapeutic or diagnostic benefit a murine antibody could have. Therefore, these murine antibodies are unsuitable for administration to a patient to detect deposits of amyloid fibrils in a patient. Thus, the present disclosure provides compositions and methods for detecting and/or monitoring amyloid deposition diseases that is less likely to produce an immunogenic HAMA response in a patient following administration.

Humanized and Chimeric Anti-Fibril Antibodies

The present disclosure provides compositions comprising humanized and chimeric antibodies or antigen-binding fragments thereof having linked thereto a detectable molecule. The disclosed compositions are useful for imaging the location and amount of amyloid deposits in a subject. Typically, an antibody consists of four polypeptides: two identical copies of a heavy (H) chain polypeptide and two copies of a light (L) chain polypeptide. Typically, each heavy chain contains one N-terminal variable ($V_H$) region and three C-terminal constant (CH1, CH2 and CH3) regions, and each light chain contains one N-terminal variable ($V_L$ or $V_K$) region and one C-terminal constant (CL) region. Each variable domain of the light and heavy chain in an antibody also comprises three segments called complementarity-determining regions ("CDR") or hypervariable regions. Each CDR in a light chain, together with the corresponding CDR in the adjacent heavy chain, form an antigen-binding site of the antibody. The variable regions of each pair of light and heavy chains form the antigen binding site of an antibody, whereas the constant region provides structural support and modulates the immune response initiated by the antigen binding.

Chimeric antibodies incorporate the variable region of a non-human antibody into the constant region of a human antibody. A chimeric 11-1F4 antibody, for instance, may be created by expressing the murine variable region with the Fc region of a human antibody, such as a human IgG1.

Humanized forms of non-human (e.g., murine) antibodies can be obtained, which contain minimal sequences derived from non-human immunoglobulin. In general, a humanized antibody may comprise one or two or more variable domains in which variable regions are derived from non-human immunoglobulin and framework regions (FR) correspond to a human immunoglobulin sequence. Thus, in some embodiments, a humanized anti-AL antibody comprises a human antibody framework region. Such antibodies can be prepared by known techniques.

The murine 11-1F4 monoclonal antibody is an anti-AL antibody produced by the SP2/0 hybridoma cell deposited by Alan Solomon, MD (University of Tennessee Medical Center at Knoxville, TN). The hybridoma cell line is available from the American Type Culture Collection (ATCC access PTA-105). The $V_K$ region (SEQ ID NO: 36) and the VH region (SEQ ID NO: 35) of the 11-1F4 antibody are shown in Table 1 below. The CDR sequences for the heavy and light chains and provided in Table 2.

TABLE 1

11-1F4 monoclonal antibody variable sequences

SEQ ID NO: 36
$V_K$ region:
Asp Val Val Met Thr Gln Thr Pro Leu Ser Leu Pro
Val Ser Leu Gly Asp Gln Ala Ser Ile Ser Cys Arg
Ser Ser Gln Ser Leu Val His Arg Asn Gly Asn Thr

TABLE 1-continued 11-1F4 monoclonal antibody variable sequences

Tyr Leu His Trp Tyr Leu Gln Lys Pro Gly Gln Ser
Pro Lys Leu Leu Ile Tyr Lys Val Ser Asn Arg Phe
Ser Gly Val Pro Asp Arg Phe Ser Gly Ser Gly Ser
Gly Thr Asp Phe Thr Leu Lys Ile Ser Arg Val Glu
Ala Glu Asp Leu Gly Leu Tyr Phe Cys Phe Gln Thr
Thr Tyr Val Pro Asn Thr Phe Gly Gly Gly Thr Lys
Leu Glu Ile Lys

SEQ ID NO: 35
$V_H$ region:
Gln Val Gln Leu Lys Glu Ser Gly Pro Gly Leu Val
Ala Pro Ser Gln Ser Leu Ser Ile Thr Cys Thr Val
Ser Gly Phe Ser Leu Ser Ser Tyr Gly Val Ser Trp
Val Arg Gln Pro Pro Gly Lys Gly Leu Glu Trp Leu
Gly Val Ile Trp Gly Asp Gly Ser Thr Asn Tyr His
Pro Asn Leu Met Ser Arg Leu Ser Ile Ser Lys Asp
Ile Ser Lys Ser Gln Val Leu Phe Lys Leu Asn Ser
Leu Gln Thr Asp Asp Thr Ala Thr Tyr Tyr Cys Val
Thr Leu Asp Tyr Trp Gly Gln Gly Thr Ser Val Thr
Val Ser Ser The complementarity determining regions (CDRs) of the variable sequences are shown in boldface type in the table above.

TABLE 2

11-1F4 monoclonal antibody CDR sequences

| Sequence | Amino Acid |
|---|---|
| CDRL1 (SEQ ID NO: 49) | Arg Ser Ser Gln Ser Leu Val His Arg Asn Gly Asn Thr Tyr Leu His |
| CDRL2 (SEQ ID NO: 50) | Lys Val Ser Asn Arg Phe Ser |
| CDRL3 (SEQ ID NO: 51) | Phe Gln Thr Thr Tyr Val Pro Asn Thr |
| CDRH1 (SEQ ID NO: 52) | Ser Tyr Gly Val Ser Trp |
| CDRH2 (SEQ ID NO: 53) | Val Ile Trp Gly Asp Gly Ser Thr Asn Tyr His Pro Asn Leu Met Ser Arg Leu Ser Ile Ser |
| CDRH3 (SEQ ID NO: 54) | Leu Asp Tyr |

One can clone the genes for the $V_H$ and $V_K$ regions shown above to produce a chimeric 11-1F4 antibody using known human antibody sequences. The chimeric 11-1F4 antibody binds to an epitope expressed by the R-pleated sheet configuration of amyloids, just as its murine counterpart does, but surprisingly, as shown in Example 6 below, the chimeric antibody binds to AL amyloid fibrils with higher affinity than the 11-1F4 mouse antibody from which it was derived.

One can also clone the genes for the CDR regions to produce a humanized form of the antibody using known human antibody sequences. Like the chimeric form of the 11-1F4 antibody, the humanized form may also have a binding affinity for amyloid fibrils that is higher than that of the murine counterpart.

Those of skill in the art will understand that the disclosed humanized and chimeric antibodies may utilize all different types of human constant regions and/or framework regions. For example, the disclosed humanized and chimeric antibodies may comprise the constant regions and/or framework regions of a human IgG (including IgG1, IgG2, IgG3, and IgG4), IgA, IgE, IgH, or IgM. In preferred embodiments, the disclosed humanized or chimeric 11-1F4 antibody comprises a human IgG1 constant region.

In some embodiments, the disclosed antibodies may comprise one or more substitutions, insertions, or deletions, so long as the antibody maintains the ability to bind to amyloid fibrils (e.g., kappa and/or lambda light chain fibrils). For example, in some embodiments, a chimeric 11-1F4 antibody of the present disclose may comprise heavy and light chains with about 85%, about 86%, about 87%, about 88%, about 89%, about 90%, about 91%, about 92%, about 93%, about 94%, about 95%, about 96%, about 97%, about 98%, about 99%, or about 100% identity compared to the corresponding heavy and light chain sequences disclosed herein, so long as the antibody maintains the ability to bind to amyloid fibrils. In some embodiments, a humanized 11-1F4 antibody of the present disclose may comprise CDRs that have about 85%, about 86%, about 87%, about 88%, about 89%, about 90%, about 91%, about 92%, about 93%, about 94%, about 95%, about 96%, about 97%, about 98%, about 99%, or about 100% identity compared to the corresponding CDR sequences disclosed herein, so long as the antibody maintains the ability to bind to amyloid fibrils.

Abbreviations

Dulbecco's Modified Eagles Medium (DMEM), Fetal Bovine Serum (FBS), ribonucleic acid (RNA); messenger RNA (mRNA); deoxyribonucleic acid (DNA); copy DNA (cDNA); polymerase chain reaction (PCR); minute (min); second (sec); Tris-borate buffer (TBE).

Amino acids are represented by the IUPAC abbreviations, as follows: Alanine (Ala), Arginine (Arg), Asparagine (Asn), Aspartic acid (Asp), Cysteine (Cys), Glutamine (Gin), Glutamic acid (Glu), Glycine (Gly), Histidine (His), Isoleucine (lie), Leucine (Leu), Lysine (Lys), Methionine (Met), Phenylalanine (Phe), Proline (Pro), Serine (Ser), Threonine (Thr), Tryptophan (Trp), Tyrosine (Tyr), Valine (Val). Similarly for nucleotides: Adenine (A), Cytosine (C), Guanine (G), Thymine (T), Uracil (U), Adenine or Guanine (R), Cytosine or Thymine (Y), Guanine or Cytosine (S), Adenine or Thymine (W), Guanine or Thymine (K), Adenine or Cytosine (M), Cytosine or Guanine or Thymine (B), Adenine or Guanine or Thymine (D), Adenine or Cytosine or Thymine (H), Adenine or Cytosine or Guanine (V), and any base (N).

Humanized or Chimeric Antibodies

To produce the chimeric antibodies of the invention, the murine 11-1F4 monoclonal antibody heavy and kappa light chain variable region genes described in U.S. Pat. No. 8,105,594 were PCR modified to facilitate the expression of the chimeric 11-1F4 antibody in mammalian cells. A detailed sequence analysis of the modified variable region genes was performed. The modified variable region genes were cloned into the appropriate mammalian expression vectors, creating the constructs 11-1F4VHpG1D200 and 11-1F4VK.pKN100. A single supervector construct, pG1KD200-11-1F4, was made from the 11-1F4VHpG1D200 and 11-IF4VK.pKN100 constructs by EcoRI restriction enzyme digest and ligation. Finally, the chimeric 11-1F4 antibody was transiently expressed in COS cells by both cotransfection and single supervector transfection. While COS cells were chosen for the co-transfection or transfection as a matter of convenience, those of skill in the art would recognize that other mammalian cell lines could be used. The characterization of the binding capacity of the chimeric 11-1F4 antibody for amyloid fibrils was determined by direct binding ELISA. Unexpectedly and beneficially, the chimeric 11-1F4 antibody bound to amyloid fibrils with higher affinity than the murine 11-1F4 antibody.

Typically, an antibody consists of four polypeptides: two identical copies of a heavy (H) chain polypeptide and two copies of a light (L) chain polypeptide. Typically, each heavy chain contains one N-terminal variable ($V_H$) region and three C-terminal constant (CH1, CH2 and CH3) regions, and each light chain contains one N-terminal variable ($V_L$ or $V_K$) region and one C-terminal constant (CL) region. The variable regions of each pair of light and heavy chains form the antigen binding site of an antibody.

An antibody useful in the compositions and methods of the invention may be a chimeric mouse-human monoclonal antibody comprising the $V_K$ region of SEQ ID NO: 47 and the $V_H$ region of SEQ ID NO: 48 or a humanized monoclonal antibody comprising CDR sequences of SEQ ID NOs: 49-54. These antibodies bind to an epitope expressed by the β-pleated sheet configuration of amyloid fibrils. Moreover, surprisingly the antibodies bind to this epitope with higher affinity than the 11-1F4 mouse antibody from which they were derived, which comprises the $V_K$ region of SEQ ID NO: 36 and the $V_H$ region of SEQ ID NO: 35. The invention includes methods of detecting amyloid deposits in a human patient which comprises administering to the patient a diagnostically effective dose of one of the above antibodies linked to a detectable molecule in a pharmaceutically-acceptable carrier. The antibody composition may be administered by any conventional route of administration, but parenteral administration (such as intravenous) is preferred. Pharmaceutically-acceptable carriers are well-known in the art and a suitable one can be selected by one of skill in the medical field.

Figure 5:
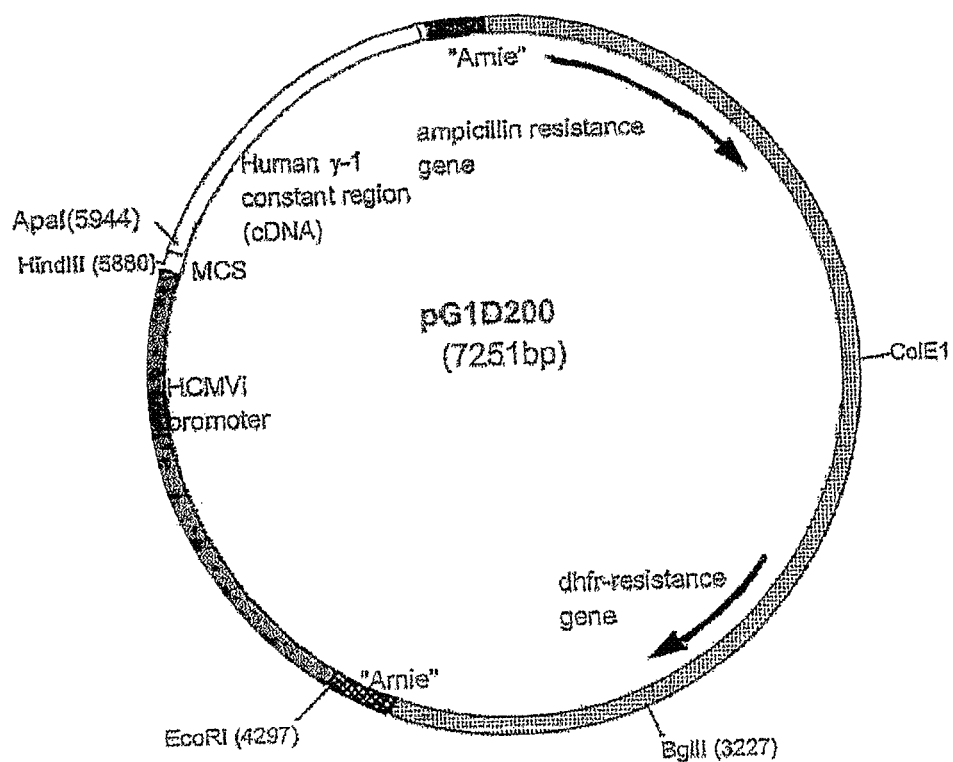
FIG. 5 is a map of the immunoglobulin gamma 1 heavy chain expression vector pG1D200. It consists of a pSV2dhfr vector fragment, which has the SV40 early and crippled SV40 late promoter, the SV40 origin, and the Co1E1 origin. It also has the ampicillin resistance and dhfr genes. The crippled SV40 late promoter drives the dhfr gene. Consequently, expression is poor, allowing for the selection of multigene/high expression level clones using comparatively low levels of methotrexate. It also has the HCMVi promoter fragment, a multiple cloning site, cDNA for a human gamma 1 constant region gene (intron minus) which is followed by a spaC2 termination signal sequence ("Amie").

Chimeric antibodies and antigen binding fragments thereof useful for the compositions and methods described and claimed herein (and a method of making the chimeric antibodies) are disclosed in co-owned Patent Cooperation Treaty application PCT/US18/399805 (with priority to U.S. patent application 62/526,835, filed Jun. 29, 2017), filed Jun. 28, 2018, and co-owned Patent Cooperation Treaty Application PCT/US2018/043374 filed Jul. 24, 2018, both of which are incorporated herein in its entirety. Materials useful to make the subject antibody include vector constructs selected from the group consisting of 11-1F4VK.pKN100 and 11-F4VH.pG1D200, shown in FIGS. 5 and 6, respectively, and the superconstruct pG.1KD20011-1F4 made from the two above vector constructs. Other useful materials include the modified murine 11-1F4 antibody $V_K$ region gene (SEQ ID NO: 42) and the modified 11-1F4 antibody $V_H$ region gene (SEQ ID NO: 45), as well as the respective primers SEQ ID NO: 41, 43, 44, and 46. The subject antibody may be made by co-transfection of the vector constructs 11-1F4VK.pKN100 and 11-F4VH.pG1D200 or the superconstruct pG.1KD20011-1F4 in a suitable mammalian host cell, such as COS (Chinese hamster ovary) cells.

Methods of making, testing, and using the humanized or chimeric 11-1F4 antibody are discussed in further detail in the Examples section below.

Diagnostic Formulations

Diagnostic compositions suitable for use in the methods described herein can include the disclosed humanized or chimeric 11-1F4 antibodies, humanized antibodies, or antigen-binding antibody fragments linked in each case to a detectable marker, and a pharmaceutically acceptable carrier or diluent.

The composition may be formulated for intravenous, subcutaneous, intraperitoneal, or intramuscular administration, although intravenous administration is preferred.

Pharmacologically acceptable carriers for various dosage forms are known in the art. For example, solvents, solubilizing agents, suspending agents, isotonicity agents, buffers, and soothing agents for liquid preparations are known. In some embodiments, the pharmaceutical compositions include one or more additional components, such as one or more preservatives, antioxidants, stabilizing agents and the like.

Sterile injectable solutions can be prepared by incorporating the marker-linked antibody or antibody fragment in the required amount in an appropriate solvent with one or a combination of ingredients enumerated above, as required, followed by sterilization microfiltration. Generally, dispersions are prepared by incorporating the diagnostic composition into a sterile vehicle that contains a basic dispersion medium and the required other ingredients from those enumerated above.

Methods of Diagnosis and Monitoring

In general, amyloidosis is caused by the buildup of an abnormal protein called amyloid. Amyloid is produced in the bone marrow and can be deposited in any tissue or organ. The specific cause of the condition depends on the type of amyloidosis.

There are several types of amyloidosis or amyloid diseases, including AL amyloidosis, AA amyloidosis, and hereditary amyloidosis.

AL amyloidosis (immunoglobulin light chain amyloidosis) is the most common type and can affect the heart, kidneys, skin, nerves and liver. Previously known as primary amyloidosis, AL amyloidosis occurs when the bone marrow produces abnormal antibodies that cannot be broken down. The antibodies are deposited in various tissues as amyloid plaques (amyloid deposits), which interfere with normal function of the tissue or organ.

AA amyloidosis generally affects the kidneys but occasionally also affects the digestive tract, liver or heart. It was previously known as secondary amyloidosis. It often occurs along with chronic infectious or inflammatory diseases, such as rheumatoid arthritis or inflammatory bowel disease.

Hereditary amyloidosis (familial amyloidosis) is an inherited disorder that usually often affects the liver, nerves, heart, and/or kidneys. Many different types of gene abnormalities present at birth are associated with an increased risk of amyloid disease or hereditary amyloidosis. The type and location of an amyloid gene abnormality can affect the risk of certain complications, the age at which symptoms first appear, and the way the disease progresses over time.

When an amyloid disease affects the heart, it can cause numerous types of complications. Amyloid deposits or plaques reduce the heart's ability to fill with blood between heartbeats. Less blood is pumped with each beat, and this may lead to shortness of breath. Amyloid deposits or plaques in or around the heart may also cause irregular heartbeats and congestive heart failure, among other organ dysfunctions When an amyloid disease affects the kidneys, it will often harm the kidneys' filtration ability, allowing protein to leak from the blood into the urine (i.e., proteinuria). Moreover, the kidneys' ability to remove waste products from your body is lowered, which may eventually lead to kidney failure.

Provided herein are methods of detecting, locating, and/or quantifying amyloid deposits in a patient suffering or suspected to be suffering from an amyloid deposition disease, such as primary (AL) amyloidosis, by administering to the patient (e.g., a human patient) a humanized or chimeric 11-1F4 antibody or an antigen-binding fragment thereof linked to a detectable marker together with a pharmaceutically acceptable carrier, in an amount effective to detect, locate, and/or quantify amyloid deposits if such are present, followed by detecting the detectable molecule bound to the amyloid deposits in the patient by diagnostic imaging to determine the extent, location, and/or amount of the amyloid deposits if such are present.

Also provided herein is a method of monitoring disease progression in a patient diagnosed with an amyloid deposition disease and having amyloid deposits comprising the steps of:

a. administering to said patient a diagnostically effective amount of a humanized or chimeric 11-1F4 antibody or an antigen-binding fragment thereof having a detectable molecule linked thereto and conducting diagnostic imaging on the patient to detect the amount of detectable molecule bound to the amyloid deposits, b. treating the patient with a therapy intended to remove amyloid deposits, such as a humanized or chimeric 11-1F4 antibody or antigen-binding fragment thereof, c. administering to said patient a diagnostically effective amount of a humanized or chimeric 11-1F4 antibody or an antigen-binding fragment thereof having a detectable molecule linked thereto and conducting diagnostic imaging on the patient to detect the amount of detectable molecule bound to the amyloid deposits, and d. comparing the detected amount of detectable molecule in step c to the detected amount of detectable molecule in step a.

The above monitoring method can be conducted starting before any treatment has taken place or can be used in the midst of a treatment regimen. That is, step a) above can be performed prior to any treatment of the patient to determine a baseline amount of amyloid deposit or step a) above can be conducted after one or more courses of treatment to determine the effect of the next succeeding course of treatment.

In some embodiments, the amyloid deposition disease (e.g., primary amyloidosis) comprises involvement of at least one organ or tissue selected from the group consisting of heart, kidneys, liver, lung, gastrointestinal tract, nervous system, muscular skeletal system, soft tissue, and skin.

In some embodiments, the disclosed methods comprise monitoring the treatment of a patient suffering from relapse or refractory ALA. In some embodiments, the patient may have kappa ALA. In some embodiments, the patient may have lambda ALA.

Exemplary diagnostic amounts can vary according to the size and health of the individual being treated, as well as the condition being diagnosed. In some embodiments, the diagnostically effective amount of a radiolabeled humanized or chimeric 11-1F4 antibody for PET is about 1-10 mCi. However, in some situations and for other diagnostic imaging modalities the dose may be higher or lower. One of skill in the diagnostic imaging art would know how to select an appropriate amount of labeled antibody or antibody fragment, as described (for example) in the references listed above.

The following examples are given to illustrate the present invention. It should be understood, however, that the invention is not to be limited to the specific conditions or details described in these examples. All printed publications referenced herein are specifically incorporated by reference.

Example 1

PCR Cloning and DNA Sequencing of the Mouse 11-1F4 Antibody

The murine 11-1F4 monoclonal antibody heavy and light chain variable region genes were PCR cloned and a detailed sequence analysis of all variable region genes isolated (both pseudo and functional) was performed. Detailed DNA and amino acid sequences of the murine 11-1F4 antibody heavy and light chain variable region genes were obtained.

Materials

Media components and all other tissue culture materials were obtained from Life Technologies (UK). The RNA solution kit was obtained from Stratagene (USA), while the first strand cDNA synthesis kit was purchased from Pharmacia (UK). All the constituents and equipment for the RCR-reaction, including AmpliTaq® DNA polymerase, were purchased from Perkin Elmer (USA). The TOPO TA Cloning® kit was obtained from Invitrogen (USA). Agarose (UltraPure™) was obtained from Life Technologies (UK). The ABI PRISM® Big Dye™ terminator cycle sequencing ready reaction kit pre-mixed cycle sequencing kit and the ABI PRISM® 310 sequencing machine were both purchased from PE Applied Biosystems (USA). All other molecular biological products were obtained from New England Biolabs (USA) and Promega (USA).

Methods

The strategy used to PCR clone the murine $V_H$ and $V_K$ genes from the hybridoma cell lines producing the murine monoclonal antibody 11-1F4 is outlined in FIG. 1.

Two clones (B2C4 and B2D6) of the SP2/0 hybridoma cell line producing the α-human light chain monoclonal antibody 11-1F4, were kindly provided by Alan Solomon, MD (University of Tennessee Medical Center at Knoxville, TN). The hybridoma cell line is available from the American Type Culture Collection (ATCC access PTA-105). The cell lines were cultured using DMEM media supplemented with 20% (v/v) FBS, penicillin/streptomycin and L-Glutamine. Cells were cultured until a total viable cell count of $10^8$ cells was reached.

The cells were harvested separately from each clone as follows. The mouse hybridoma cell line was grown in suspension in an appropriate culture medium and in sufficient quantities to provide a total viable cell count of about $10^8$ cells. The culture supernatant was harvested and the hybridoma cells pelleted in a bench top centrifuge (250 g, 5 min). The cells were gently re-suspended in 20 ml PBS and a 100 μl aliquot was taken for a viable cell count. The cells in the aliquot were pelleted once more and 200 μl of PBS and 200 μl of trypan blue were added to the 100 μl of cells and mixed gently. Ten μl of this mixture was pipetted into a disposable cell-counting slide and the number of white cells in 9 small squares was counted under a microscope. Blue cells (i.e., dead cells) were not counted. The count process was repeated, the results averaged, and the average results multiplied by $9\times10^5$ to obtain a viable cell count for the cells in 20 ml PBS. Once sufficient cells had been harvested, they were re-suspended in 10 ml of Solution D for RNA isolation (see below, Stratagene RNA Isolation Kit).

Total RNA was then isolated separately from the cells of each clone using a Stratagene RNA isolation kit, according to the manufacturer's instructions. One ml of 2 M sodium acetate (pH 4.0) was added to the sample and the contents of the tube were thoroughly mixed by repeatedly inverting the tube. To the tube was added 10.0 ml of phenol (pH 5.3-5.7) and the contents again mixed thoroughly by inversion. To the mixture was added 2.0 ml of chloroform-isoamyl alcohol mixture, the tube was capped and vigorously shaken for 10 seconds, and the tube was incubated in ice for 15 minutes. The sample was transferred to a 50-ml thick-walled, round-bottom centrifuge tube that had been pre-chilled on ice and the tube was spun in a centrifuge at 10,000×g for 20 minutes at 4° C. Two phases were visible in the tube after centrifugation. The upper, aqueous phase contained the RNA, while the lower phenol phase and interphase contained DNA and proteins. The RNA-containing upper, aqueous phase was transferred to a fresh centrifuge tube and the lower phenol phase was discarded. An equal volume of isopropanol was added to the aqueous phase and the contents mixed by inversion, following which the tube was incubated for 1 hour at −20° C. to precipitate the RNA. The tube was spun in a centrifuge at 10,000×g for 20 minutes at 4° C. After centrifugation, the pellet at the bottom of the tube, which contains the RNA, was removed and the supernatant discarded. The pellet was dissolved in 3.0 ml of solution D, 3.0 ml of isopropanol was added to the tube and the contents mixed well. After incubating the tube for 1 hour at −20° C., it was again spun in a centrifuge at 10,000×g for 10 minutes at 4° C. and the supernatant removed from the tube and discarded. (Note: Up to this point, the RNA had been protected from ribonucleases by the presence of guanidine isothiocyanate but was now no longer protected.) The pellet was washed with 75% (v/v) ethanol (DEPC-treated water (25%)) and the pellet was dried under vacuum for 2-3 minutes. The RNA pellet is re-suspended in 0.5-2 ml of DEPC-treated water.

Following the manufacturer's instructions, an Amersham Pharmacia Biotech first strand cDNA synthesis kit was employed to produce a single-stranded DNA copy of the 11-1F4 hybridoma mRNA using the Not I-d(T)$^{18}$ primer supplied with the kit. One reaction was performed for each of the two RNA samples isolated, as follows. The components used were: Bulk first strand cDNA reaction mix, Cloned FPLCpure™ Murine Reverse Transcriptase, RNA-guard™, BSA, dATP, dCTP, dGTP, and dTTP, 200 mM DIT aqueous solution, Not I-d(T)$^{18}$ primer: 5' d[AACTG-GAAGAATTCGCGGCCGCAGGAA$_{18}$]-3', and DEPC treated water.

Approximately 5 μg of total RNA in 20 μl DEPC water was heated to 65'C for 10 min and then chilled on ice. The bulk first strand cDNA reaction mix was pipetted gently to obtain a uniform suspension and the reaction set up in a 0.5 ml microcentrifuge tube as below. 20 μl denatured RNA solution, 11 μl Bulk first strand cDNA reaction mix, 1 μl Not I-d(T)$^{18}$ primer, and 1 ul DTT solution for 33 μl total volume. The reactants were mixed gently by pipetting and incubated 37° C. for 1 hour.

The murine heavy and kappa light chain variable region genes ($V_H$ genes and $V_K$ genes, respectively) were then PCR amplified from the ssDNA template using the method described by Jones and Bendig (*Bio/Technology* 9:88).

Separate PCR reactions were prepared for each of the degenerate leader sequence specific primers (MHVI-MHV12 for $V_H$ and MKVI-MKV11 for $V_K$) with the appropriate constant region primer (an equimolar mix of MHCI-MHC3 for $V_H$ and MKC for $V_K$). Tables I & 2 detail the primers used to amplify the $V_H$ and $V_K$ region genes, respectively. In total, 12 heavy chain reactions and 11 kappa light chain reactions were performed. AmpliTaq® DNA polymerase was used to amplify the template cDNA in all cases, as follows.

The completed cDNA first strand synthesis reaction was heated at 90° C. for 5 minutes to denature the RNA-cDNA duplex and inactivate the reverse transcriptase and chilled on ice. Eleven GeneAmp™ PCR reaction tubes were labeled MKV1-11. For each tube a 100 µl reaction mixture was prepared, each reaction mixture containing 69.3 µl of sterile water, 10 µl of 10×PCR buffer II, 6 µl of 25 mM MgCl₂, 2 µl each of the 10 mM stock solutions of dNTPs, 2.5 µl of 10 mM MKC primer, 2.5 µl of one of the 10 mM MKV primers and 1 µl of RNA-cDNA template mix. To each of the tubes was then added 0.7 µl of AmpliTaq® DNA polymerase and the completed reaction mix overlaid with 50 µl of mineral oil.

A similar series of reaction mixes was prepared as described above to PCR-clone the mouse heavy chain variable region gene. However, this time twelve reaction tubes were labeled and one of the twelve MHV primers and the appropriate MHC primer were added to each. That is, to PCR-amplify the variable domain gene of a mouse γ1 heavy chain, for example, the MHC G1 primer was used.

The reaction tubes were loaded into a DNA thermal cycler and cycled (after an initial melt at 94° C. for 1.5 min) at 94° C. for 1 min, 50° C. for 1 min and 72° C. for 1 min over 25 cycles. The last cycle was followed by a final extension step at 72° C. for 10 min before cooling to 4° C. Except for between the annealing (50° C.) and extension (72° C.) steps when an extended ramp time of 2.5 min was used, a 30 sec ramp time was used between each step of the cycle. A 10 µl aliquot from each PCR reaction was run on a 1% (w/v) agarose/1×TBE buffer gel containing 0.5 µg/ml ethidium bromide to determine which of the leader primers produced a PCR-product. Positive PCR-clones were about 420-500 bp in size.

The above PCR-amplification process was repeated twice more and those PCR-reactions that appeared to amplify full-length variable domain gene were selected. A 6 µl aliquot of each potential PCR-product was directly cloned into the pCR™II vector provided by the TA Cloning® kit, as described in the manufacturers instructions. Aliquots of 10.0% (v/v), 1.0% (v/v) and 0.1% (v/v) aliquots of the transformed *E. coli* cells were pipetted onto individual 90 mm diameter LB agar plates containing 50 µg/ml ampicillin, overlaid with 25 µl of the X-Gal stock solution and 40 µl of IPTG stock solution, and incubated overnight at 37° C. Positive colonies were identified by PCR-screening.

TABLE 1

PCR primers for cloning mouse kappa light chain variable region genes

| Name | Sequence (5'→3') | SEQ ID NO: |
|---|---|---|
| MICV1 (31mer) | ATGAAGATTGCCTGTTAGGCTGTTGGTGCTG | 1 |
| MKV2 (30mer) | ATGGAGWCAGACACACTCCTGYTATGGGTG | 2 |
| MKV3 (30mer) | ATGAGTGTGCTCACTCAGGTCCTGGSGTTG | 3 |
| MKV4 (33mer) | ATGAGGRCCCCTGCTCAGWTTYTTGGMWTCTTG | 4 |
| MKV5 (30mer) | ATGGATTTWCAGGTGCAGATTWTCAGCTTC | 5 |
| MKV6 (29mer) | ATGAGGTKCYYTGYTSAYCTYCTCTGRGG | 6 |
| MKV7 (32mer) | ATGGGCWTCAAAGATGGAGTCACAKWYYCWGG | 7 |
| MKV8 (30mer) | ATGTGGGGAYCTKTTTYCMMTTTTTCAATG | 8 |
| MKV9 (25mer) | ATGGTRTCCWCASCTCAGTTCCTTG | 9 |
| MKV10 (27mer) | ATGTATATATGTTTGTTGTCTATTTCT | 10 |
| MKV11 (28mer) | ATGGAAGCCCCAGCTCAGCTTCTCTTCC | 11 |
| MKC (20mer) | ACTGGATGGTGGGAAGATGG | 12 |

TABLE 2

PCR primers for cloning mouse heavy chain variable region genes

| Name | Sequence (5'→3') | SEQ ID NO: |
|---|---|---|
| MHV1 (27mer) | ATGAAATGCAGCTGGGGCATSTTCTTC | 13 |
| MHV2 (26mer) | ATGGGATGGAGCTRTATCATSYTCTT | 14 |
| MHV3 (27mer) | ATGAAGWTGTGGTTAAACTGGGTTTTT | 15 |
| MHV4 (25mer) | ATGRACTTTGGGYTCAGCTTGRTTT | 16 |
| MHV5 (32mer) | ATGGGACTCCAGGCTTCAATTTAGTTTTCCTT | 17 |
| MHV6 (29mer) | ATGGCTTGTCYTTRGSGCTRCTCTTCTGC | 18 |
| MHV7 (27mer) | ATGGRATGGAGCKGGRTCTTTMTCTT | 19 |

TABLE 2-continued

PCR primers for cloning mouse heavy chain variable region genes

| Name | Sequence (5'→3') | SEQ ID NO: |
|---|---|---|
| MHV8 (23mer) | ATGAGAGTGCTGATTCTTTTGTG | 20 |
| MHV9 (31mer) | ATGGMTTGGGTGTGGAMCTTGCTTATTCCTG | 21 |
| MHV10 (28mer) | ATGGGCAGACTTACCATTCTCATTCCTG | 22 |
| MHV11 (28mer) | ATGGATTTTGGGCTGATTTTTTTTATTG | 23 |
| MHV12 (27mer) | ATGATGGTGTTAAGTCTTCTGTACCTG | 24 |
| MHCG1 (21mer) | CAGTGGATAGACAGATGGGGG | 25 |
| MHCG2a (21mer) | CAGTGGATAGACCGATGGGGG | 26 |
| MHCG2b (21mer) | CAGTGGATGAGCTGATGGGGG | 27 |
| MHCG3 (21mer) | CAAGGGATAGACAGATGGGGC | 28 |

Five μl aliquots from each PCR reaction were run on a 1% agarose/TBE (pH 8.8) gel to determine which had produced a PCR product of the correct size (ca. 450 bp). Those putative positive PCR products so identified were directly cloned into the pCR2.1 vector provided by the TA Cloning® kit and transformed into TOP10 competent cells as described in the manufacturer's protocol. Colonies containing the plasmid with a correctly sized insert were identified by PCR-screening the colonies using the 1212 and 1233 oligonucleotide primers (Table 3) according to the method of Gussow and Clackson (*Nucleic Acids Res.* 17:4000). Those putative positive clones so identified were double-stranded plasmid DNA sequenced using the ABI PRISM 310 Genetic Analyzer and the ABI PRISM BigDye™ terminator. Three positive clones each of the $V_H$ and $V_K$ genes from the B2C4 hybridoma cell line clone were sequenced, as were four positive clones of the $V_K$ gene and six of the $V_H$ gene from the B2D6 hybridoma cell line clone.

TABLE 3

Primers for PCR screening and sequencing transformed colonies

| Name | Sequence (5'→3') | SEQ ID NO: |
|---|---|---|
| 1212 (17mer) | GTTTTCCCAGTCACGAC | 29 |
| 1233 (21mer) | AGCGGATAATTTCACACAGGA | 30 |

The results of the 12 PCR reactions performed for each hybridoma clone (B2C4 and BCD6) to amplify the murine 11-1F4 antibody heavy chain variable region gene are presented in Table 4(a).

The degenerate leader sequence primer MHV7, in combination with a mix of the MHCGI-3 constant region primers (Table 1), yielded a PCR product of about 600 bp from template cDNAs derived from both the B2C4 and B2D6 hybridoma cell lines. Since this band was larger than the expected size for an average $V_H$ gene (450 bp), it was not investigated further. Conversely, the degenerate leader sequence primer MHV6, in combination with a mix of the MHCGI-3 constant region primers (Table 1), yielded a PCR product of the expected size (450 bp) for a $V_H$ gene from template cDNA derived from both the B2C4 and B2D6 hybridoma cell lines.

Table 4 shows the results of the PCR amplifications performed to clone the murine 11-1F4 monoclonal antibody variable region heavy (a) and light (b) chain genes from the SP2/0 hybridoma cell lines B2C4 and B2D6. Column three contains a record of the actual PCR results. Where a band was observed for a particular combination of primers its size in base pairs (bp) was recorded in the appropriate space.

TABLE 4

Results of PCR amplification (a)

| $C_H$ Region Primer | Leader Primer | Approximate Band Size (bp) | |
|---|---|---|---|
| | | B2C4 | B2D6 |
| MHCG1-3 (mix) | MHV1 | | |
| " | MHV2 | | |
| " | MHV3 | | |
| " | MHV4 | | |
| " | MHV5 | | |
| " | MHV6 | 450 | 450 |
| " | MHV7 | 600 | 600 |
| " | MHV8 | | |
| " | MHV9 | | |
| " | MHV10 | | |
| " | MHV11 | | |
| " | MHV12 | | |

(b)

| $C_K$ Region Primer | Leader Primer | Approximate Band Size (bp) | |
|---|---|---|---|
| | | B2C4 | B2D6 |
| MKC | MKV1 | 450 | 450 |
| " | MKV2 | <450 | <450 |
| " | MKV3 | | |

TABLE 4-continued

Results of PCR amplification

| | | |
|---|---|---|
| " | MKV4 | |
| " | MKV5 | |
| " | MKV6 | 200 |
| " | MKV7 | |
| " | MKV8 | |
| " | MKV9 | |
| " | MKV10 | |
| " | MKV11 | |

Sequence analysis of three clones from the B2C4 derived PCR product and five clones from the B2D6 derived PCR product revealed a single heavy chain variable region sequence (FIG. 2).

The cloning strategy used (amplification of the entire variable region gene by using primers which flank this region, i.e., leader sequence and constant region sequence specific primers) allowed the complete FR1 sequence to be identified. All eight clones sequenced had identical sequence in this region (FIG. 2).

The results of the 11 PCR reactions performed for each hybridoma clone (B2C4 and BCD6) to amplify the murine 11-1F4 antibody kappa light chain variable region gene are presented in Table 4(b).

The degenerate leader sequence primer MKV6 in combination with the MKC constant region primer (Table 2), produced a PCR product of about 200 bp from template cDNA derived from the B2C4 hybridoma cell line only. Since this band was much smaller than the expected size for a $V_K$ gene (450 bp), it was not investigated further.

The degenerate leader sequence primer MKV2, in combination with the MKC constant region primer (Table 2), produced a PCR product which was smaller than the expected 450 bp band (when viewed on an agarose gel) from template cDNA derived from both the B2C4 and B2D6 hybridoma cell lines. In addition, previous $V_K$ cloning had found that the MKV2 primer amplified a well known kappa light chain pseudogene. Therefore, sequence analysis of one clone of each PCR product was performed in order to confirm that this product was a pseudogene and not the murine 11-1F4 antibody $V_K$ gene. This sequence analysis revealed that this PCR clone was indeed the pseudogene.

Finally, the degenerate leader sequence primer MKV1, in combination with the MKC constant region primer (Table 1), produced a PCR product of about the expected size (450 bp) for a $V_K$ gene, from template cDNA derived from both the B2C4 and B2D6 hybridoma cell lines.

Sequence analysis of three clones of the B2C4 derived PCR product and four clones of the B2D6 derived PCR product revealed a single kappa light chain variable region sequence which could not be identified as a pseudogene.

Thus, the 11-1F4 antibody heavy chain variable region gene was cloned (using constant region specific and leader sequence specific primers) from the hybridoma mRNA and sequenced.

When translated, the sequence gave a TVSS peptide sequence. Analysis of 122 rearranged human $V_H$ genes, recorded in the Kabat database (Kabat et al.—*Sequences of Proteins of Immunological Interest*), revealed that 84% of these sequences had a TVSS peptide sequence. It was therefore concluded that the $V_H$ gene isolated was the correct 11-1F4 antibody gene sequence.

The murine 11-1F4 antibody variable region kappa light chain gene was also successfully cloned and sequenced, as was a non-functional $V_K$ pseudogene gene. This pseudogene was first identified by Carroll et al (*Molecular Immunology* (1988) 25:991). The sequence arises from an aberrant mRNA transcript which is present in all standard fusion partners derived from the original MOPC-21 tumor (including SP2/0). As a result of the aberrant mRNA, the invariant cysteine at position 23 is replaced by a tyrosine residue, and the VJ joint is out of frame, resulting in a stop codon at position 105.

It is common for lymphoid or hybridoma cells to synthesize more than one rearranged light immunoglobulin mRNA. These mRNAs are usually non productive due to the presence of termination codons or frame shifts not usually seen in functional $V_K$ genes. These pseudo messengers often present major problems when cloning immunoglobulin genes from hybridomas because they are very good substrates for V region PCR, despite the fact that they do not encode functional polypeptides.

The 11-1F4 antibody $V_K$ gene sequence was identified after detailed sequence analysis of seven separate PCR clones, isolated from two different PCR products to yield SEQ. ID NO: 36. Since all sequences were identical, it was accepted as the correct 11-1F4 antibody kappa light chain variable region sequence.

The cloned $V_H$ and $V_K$ region genes were used to make the chimeric mouse-human 11-1F4 monoclonal antibody, which was then be analyzed to confirm specific binding to AL fibrils.

Example 2

Construction of Chimeric Mouse-Human 11-1F4 (c11-1F4) Antibody

In order to allow transient expression of the 11-1F4 $V_H$ and $V_K$ variable region genes described above in mammalian cells as part of a chimeric mouse-human antibody, it was necessary to modify the 5'- and 3'-ends using specifically designed PCR primers (Table 5). The oligonucleotide primers F39836 and F39837 were used to PCR modify the 11-1F4 $V_K$ gene, while primers F39835 and F58933 were used to PCR modify the 11-1F4 $V_H$ gene. The back (BAK) primers F39836 and F39835 introduced a HindIII restriction site, a Kozak translation initiation site, and an immunoglobulin leader sequence to the 5' ends of the $V_K$ and $V_H$ genes respectively. The forward (FOR) oligonucleotide primer F39837 introduced a splice donor site and a BamHI restriction site to the 3' end of the $V_K$ gene while the forward (FOR) oligonucleotide primer F58933 appended the first 22 base pairs of the gamma-1CH$_1$ gene including an ApaI restriction site to the 3' end of the $V_H$ gene.

TABLE 5

Oligonucleotide primers used to PCR modify the 11-1F4 heavy and kappa light chain variable region genes

| Name | Sequence (5'→3') | SEQ ID NO: |
|---|---|---|
| F39835 VH BAK | AAGCTTGCCGCCACCATGGCTGTCCTGGGGCTGCTCITCTGC | 31 |
| F58933 VH FOR | CCGATGGGCCCTTGGTGGAGGCTGAGGAGACGGTGACTGAGGTTCC | 32 |
| F39836 VK BAK | AAGCTTGCCGCCACCATGAAGTTGCCTGTTAGGCTGTTGGTGC | 33 |
| F39837 VK FOR | GGATCCACTCACGTTTGATTTCCAGCTTGGTCCCCCCTCCGA | 34 |

The Kozak consensus sequence is crucial to the efficient translation of a variable region sequence (Kozak—*J Mol Bio* 196:947). It defines the correct AUG codon from which a ribosome commences translation, and the single most critical base is the adenine (or less preferably, a guanine) at position −3, upstream of the AUG start.

The immunoglobulin leader sequence ensures that the expressed antibody is secreted into the medium and therefore is easily harvested and purified. The leader sequences used in this instance were the murine 11-1F4 $V_K$ and $V_H$ leader sequences cloned from the hybridoma cDNA during the $V_H$ and $V_K$ cloning process.

The splice donor sequence is important for the correct in-frame attachment of the light chain variable region to its appropriate constant region, thus splicing out the 130 bp $V_K$:$C_K$ intron. The heavy chain variable region was attached directly to its appropriate constant region gene via the ApaI site, thus eliminating the need for a splice donor site.

The sub-cloning restriction sites HindIII and BamHI, and HindIII and ApaI, respectively, bracket the modified $V_K$ and $V_H$ variable region genes, while the use of different unique restriction sites ensured directional sub-cloning into the appropriate mammalian expression vector.

The 11-1F4 light chain variable region gene was first carefully analyzed to identify any unwanted splice donor sites, splice acceptor sites, and Kozak sequences (see Table 6). Both the heavy and light chain variable region genes were analyzed for the presence of any extra sub-cloning restriction sites which would later interfere with the sub-cloning and/or expression of functional whole antibody. None were found.

Separate PCR reactions were prepared as follows, one for each variable region gene. The plasmids 11-1F4 $V_H$.pCR2.1 and 11-1F4 $V_K$.pCR2.1 described above were used as templates. A 100 μl reaction mixture was prepared in each PCR tube, each mixture containing up to 41 μl of sterile water, 10 μl of 10×PCR buffer I, 8 μl of the 10 mM stock solution of dNTPs, 1 μl of 10 mM of 5' forward primer, 1 μl of the 10 mM 3' Reverse primer, and 1 μl of a ⅒ dilution of template DNA. Finally, 0.5 μl of AmpliTaq® DNA polymerase (2.5 units) was added before overlaying the completed reaction mixture with 50 μl of mineral oil. The reaction tubes were loaded into a DNA thermal cycler and cycled (after an initial melt at 94° C. for 1 min) at 94° C. for 30 sec, 68° C. for 30 sec and 72° C. for 50 sec over 25 cycles. The completion of the last cycle was followed with a final extension step at 72° C. for 7 min before cooling to 4° C. A 10 μl aliquot from each PCR reaction tube was run on a 1.2% (w/v) agarose/1×TBE buffer gel containing 0.5 μg/ml ethidium bromide to determine size and presence of a PCR-product. Positive PCR-clones were about 420 bp in size. Those putative positive PCR products so identified were directly cloned into the pCR2.1 vector, provided by the Topo TA Cloning® kit, and transformed into TOP10 competent cells as described in the manufacturer's protocol. Colonies containing the plasmid with a correctly sized insert were identified by PCR-screening the colonies using the 1212 and 1233 oligonucleotide primers (Table 3) according to the method of Gussow and Clackson. Those putative positive clones so identified were double-stranded plasmid DNA sequenced using the ABI PRISM 310 Genetic Analyzer and the ABI PRISM BigDye™ terminator. Two positive clones each of the Topo TA cloned $V_H$ and $V_K$ genes were sequenced.

TABLE 6

Sequences important for the efficient expression of immunoglobulin genes in mammalian cells

| Name | Consensus DNA Sequences |
|---|---|
| Kozak translation initiation site | CCGCCRCCAUGG |
| Kappa light chain splice donor site | AC::GTRAGT |
| Heavy chain splice donor site | AG::GTRAGT |
| Immunoglobulin splice acceptor site | YYYYYYYYYYNCAG::G |

Bases shown in bold are considered to be invariant within each consensus sequence.

Figure 4:
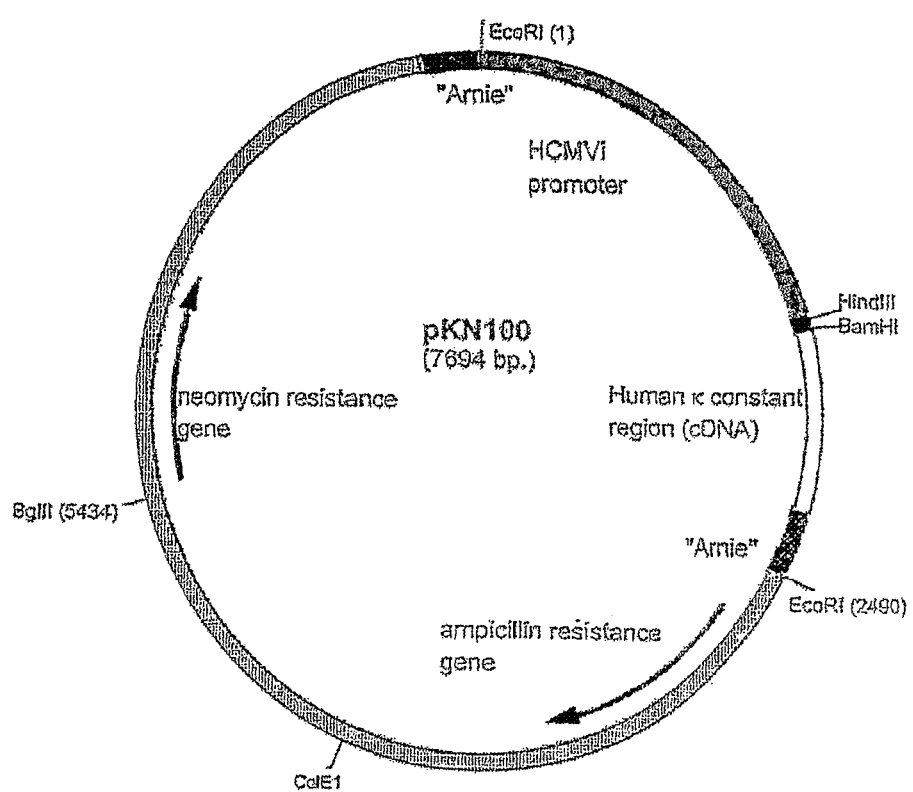
FIG. 4 is a map of the immunoglobulin kappa light chain expression vector pKN100. It consists of a pSV2 vector fragment, which has the SV40 early and crippled SV40 late promoter, the SV40 origin and the Co1E1 origin. It also has the ampicillin resistance and neo genes. The crippled SV40 late promoter drives the neo genes. It also has the HCMVi promoter, a multiple cloning site (containing the BamHI and HindIII restriction sites) for the insertion of an immunoglobulin variable region gene, and cDNA for the human kappa constant region gene terminated by a spaC2 termination signal sequence ("Arnie"), which is in the same orientation as the kappa light chain expression cassette.

Clones containing the correctly modified 11-1F4 $V_H$ and 11-1F4 $V_K$ genes were identified and the modified V genes from these clones were subcloned into their respective expression vectors to facilitate the expression of chimeric heavy and kappa light chains in mammalian cells. The modified 11-1F4 $V_K$ gene was subcloned into the expression vector pKN100 (FIG. 4) as a HindIII-BamHI fragment; this vector contains a human kappa constant region gene (allotype: Km (3 Ala153, Ser191)). The modified 11-1F4 $V_H$ gene was also subcloned as a HindIII-ApaI fragment into the expression vector pG1D200 (FIG. 5); this vector contained a human γ1 constant region gene (allotype: G1m (−1 Glu377, Met381, −2 Ala462, 3 Arg222, Ser229)). Both the kappa and γ1 constant region allotypes used are commonly found in the caucasian population. The ligated expression constructs, 11-1F4VK.pKN100 and 11-1F4VH.pG1D200, were then used to transform DH5a competent cells, and positive clones were identified using the PCR screening method discussed above with the original PCR modification primers (Table 4). The expression vectors are readily available.

Example 3

Construction of a Single Supervector for Transient Expression of Chimeric 11-1F4 in COS Cells.

A single supervector expressing both immunoglobulin chains of the chimeric 11-1F4 antibody was constructed as follows. The 11-1F4 kappa light chain expression cassette (which contained the HCMVi promoter, the 11-1F4 kappa light chain variable region gene, and the kappa light chain constant region gene) was restriction enzyme digested (EcoRI at positions 1 and 2490) out of the 11-1F4VK.pKN100 construct (FIG. 4) and subsequently ligated into the 11-1F4VHpG1D200 construct via the unique EcoRI (position 4297, FIG. 5). This ligation resulted in the construction of a supervector construct, pG1KD200-11-1F4, containing both the heavy and kappa light chains of the 11-1F4 chimeric antibody.

Example 4

Transient expression of the chimeric γ1/K.11-1F4 whole antibody in COS cells

The chimeric 11-1F4 antibody was transiently expressed in COS cells from the European Collection of Cell Cultures (ECACC) in two ways:
(i) By cotransfection of 10 μg of each of the vector constructs 11-1F4VK.pKN100 and 11-1F4VH.pG1D200. Co-transfections were carried out in duplicate.
(ii) By transfection of 13 μg of the single supervector construct pG1KD200-11-1F4. Supervector transfections were carried out five times.

The following transfection method was used. The COS cell line was grown in DMEM supplemented with 10% (v/v) FCS, 580 μg/ml L-glutamine and 50 Units/ml penicillin/50 μg/ml streptomycin ("media") in a 150 $cm^2$ flask until confluent. The cells were trypsinized, spun down in a bench top centrifuge (250 g for 5 min), then re-suspended in 6 ml of media before dividing them equally between three 150 $cm^2$ flasks, each containing 25 ml of fresh, pre-warmed media. The cells were incubated overnight at 37° C. in 5% $CO_2$ and then harvested the next day while they are still growing exponentially. Each flask contained approximately $1 \times 10^7$ cells. The cells were trypsinized again, pelleted as before, and washed in 20 ml of PBS, following which they were re-suspend in sufficient PBS to create a cell concentration of $1 \times 10^7$ cells/ml. 700 μl of these washed COS cells were pipetted into a Gene Pulser® cuvette, to which was then added 1 μl of both the heavy chain and kappa light chain expression vector DNA (each at 10 μg) or 13 μg of the super-vector construct. A 1900 Volt, 25 pFarad capacitance pulse was delivered to the mixture using the Bio-Rad Gene Pulser® apparatus. The pulsing was repeated for each experimental transfection and a "no DNA" control (in which the COS cells were electroporated in the absence of any DNA). A positive control of a previously-expressed antibody was also carried out to test the efficiency of the COS cells.

The COS cells were allowed to recover at room temperature for 10 min, then gently pipetted the into a 10 cm diameter tissue culture dish containing 8 ml of pre-warmed DMEM supplemented with 10% (v/v) γ-globulin free FBS, 580 μg/ml L-glutamine and 50 Units/ml penicillin/50 μg/ml streptomycin, and incubated in 5% $CO_2$ at 37° C. for 72 hours before harvesting the COS cell supernatant for analysis. After incubation for 72 hours the medium was collected, spun to remove cell debris and analyzed by ELISA for chimeric antibody production and antigen binding of the c11-1F4 antibody.

Example 5

Quantification of the Chimeric γ1/K 11-1F4 Antibody Via Capture ELISA

Following expression, the whole IgG molecules present in the COS cell supernatant were quantified using a capture ELISA assay. IgG molecules were captured on a Nunc-Immuno MaxiSorb™ plate via an immobilized goat anti-human IgG, Fcγ fragment-specific antibody, and detected via an anti-human kappa light chain peroxidase conjugated antibody. A standard curve was generated by capturing and detecting known concentrations of a standard IgG antibody on the same plate in the same way as follows. Each well of a 96-well immunoplate was coated with 100 μl aliquots of 0.4 μg/ml goat anti-human IgG antibody diluted in PBS and incubated overnight at 4° C. The excess coating solution was removed and the plate was washed three times with 200 μl/well of washing buffer (1×PBS, 0.1% TWEEN). Into all wells except the wells in column 2, rows B to G, was dispensed 100 μl of SEC buffer. A 1 μg/ml solution of the human IgG1/kappa antibody in SEC buffer was prepared to serve as a standard and 200 μl/well was pipetted into the wells in column 2, rows B and C. The medium from the transfected cos cells was centrifuged (250 g, 5 min), saving the supernatant. An aliquot of 200 μl of the supernatant from the "no DNA" control (in which COS cells were transfected in the absence of DNA) was pipetted into the well in column 2, row D, and aliquots of 200 μl/well of experimental supernatants were pipetted into the wells of column 2, rows E, F, and G. The 200 μl aliquots in the wells of column 2, rows B to G were mixed and then 100 μl was transferred from each well to the neighboring well in column 3. This process was continued to column 11 with a series of 2-fold dilutions of the standard, control, and experimental samples, following which all were incubated at 37° C. for 1 hour and all the wells were rinsed six times with 200 μl aliquots of washing buffer. The goat anti-human kappa light chain peroxidase conjugate was diluted 5000-fold in SEC buffer and 100 μl of the diluted conjugate added to each well, followed by a repetition of the incubation and rinsing steps. To each well was added 150 μl of K-BLUE substrate, followed by incubation in the dark at 25° C. for 10 min. The reaction was stopped by adding 50 µl of RED STOP solution to each well and the optical density was read at 655 nm.

Example 6

Binding Analysis of the Chimeric 11-1F4 Antibody

The chimeric 11-1F4 antibody was tested for binding to amyloid fibrils using a direct binding ELISA assay. Synthetic fibrils were formed from an immunoglobulin light chain protein and used to monitor the reactivity of the antibody in a solid-state ELISA-based assay using a "low-binding" polystyrene plates (Costar, #3474). Immediately prior to coating the plate, a mass of 250 µg of fibrils was diluted to 1 ml with coating buffer (0.1% bovine serum albumin in phosphate buffered saline pH 7.5). The sample was then sonicated for 20 sec using a Tekmar Sonic Disruptor sonicating probe, with the power set to 40% of maximum, resulting in a solution of short fibrils composed of up to 2-5 protofilaments each. This solution was then diluted to 5 ml, mixed well by vortex, and aliquoted into the wells of the plate. This process yielded 50 µl of fibril solution having a concentration of 50 µg/ml in each well. The plate was then dried overnight by placing it uncovered in a 37° C. incubator.

The ELISA assay was then performed as follows within 48 hours of preparing the plate. The wells were blocked by the addition of 100 µl of 1% BSA in PBS and incubated for 1 hour at room temperature on a shaker. The plate was washed ×3 in PBS, 0.05% Tween 20 (v/v). To each well of the plate was added 50 µl of a solution of c11-1F4 (3 µg/ml antibody in 0.1% BSA/PBS) and the plate incubated at room temperature for 1 hour on a shaker. The plate was again washed ×3 (as before) and detection of bound antibody was accomplished using a biotinylated goat anti-mouse IgG antibody (Sigma# B-8774, anti-heavy and light-chain).

Sequence analysis of the successfully modified $V_H$ and $V_K$ genes revealed the correct sequence was present. Detailed DNA and amino acid sequences of the modified 11-1F4 $V_K$ and $V_H$ genes are presented in FIGS. 3 & 4. The modified $V_K$ and $V_H$ genes were successfully cloned into the mammalian expression vectors pG1D200 and pKN100 respectively, and the resulting 11-1F4VK.pKN100 and 11-1F4VHpG1D200 constructs were used for cotransfection of mammalian cells.

The 11-1F4VK.pKN100 and 11-1F4VHpG1D200 constructs were also subsequently used to construct a single supervector (pG1 KD200-11-1F4), which expressed the chimeric 11-1F4 antibody in mammalian cells. The chimeric II-1F4 antibody expression levels, from both cotransfections and supervector transfections of ECACC COS cells were assayed. The expression levels observed from the pG1KD200-11-1F4 supervector transfections (10326 ng/ml) were 3.7 fold higher than the levels observed from the corresponding co-transfections of the 11-1F4VK.pKN100 and 11-1F4VHpG1D200 constructs (2820 ng/ml).

Figure 8:
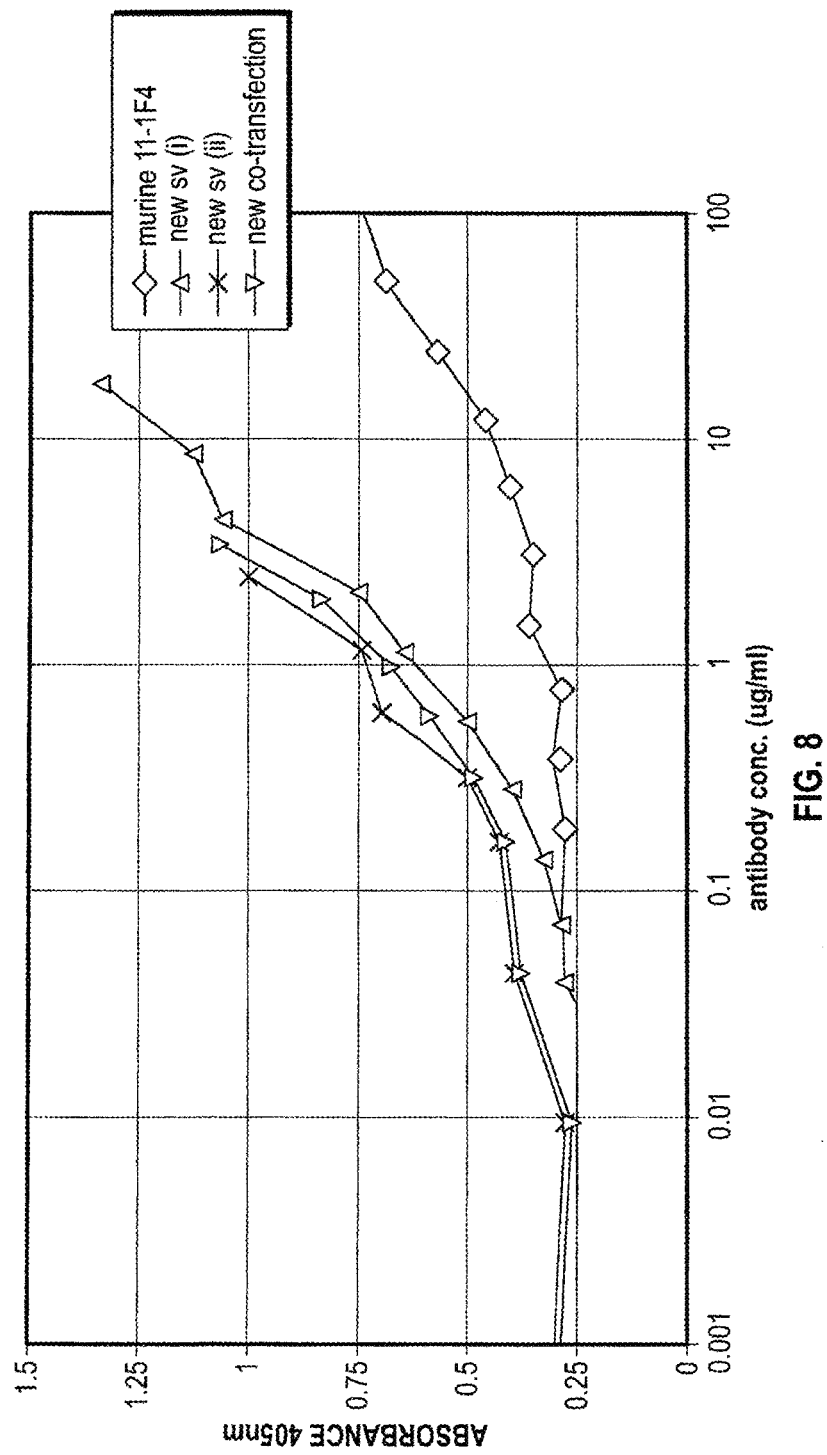
FIG. 8 is a graphical representation of the result of the amyloid fibril binding ELISA assay. The cos cell supernatants containing chimeric 11-1F4 antibody were tested separately on the same ELISA plate along with purified murine 11-1F4 antibody. The absorbance was read at OD405. New sv=pG1KD200-11-1F4. New co-transfection=11-1F4VHpG1D200 plus 11-1F4VK.pKN100.

Following expression and quantification, the chimeric 11-1F4 antibody was tested for binding to target antigen (amyloid fibrils kindly supplied by the NCI) by direct binding ELISA. The results of the binding ELISA are presented in FIG. 8. Supernatants from the two best individual pG1KD200-11-1F4 supervector transfections were assayed in parallel with one supernatant from the corresponding co-transfection.

The results indicated that the chimeric 11-1F4 antibody bound to the amyloid fibrils with a higher affinity than its murine equivalent. This result is surprising and unexpected because normally a chimeric antibody would be expected to have a binding affinity comparable to the original murine antibody. Without intending to be bound by the particular mechanism, the inventors believe it is possible that the net effect of combining the 11-1F4 murine V regions with the human yl/K C regions used to create the chimeric 11-1F4 antibody produced an antibody of higher affinity.

Samples of CHO cells (identified as CAEL-101) that secrete one embodiment of the chimeric 11-1F4 monoclonal antibody (which embodiment is sometimes referred to herein as CAEL-101 or as the antibody CAEL-101) used herein were deposited with the American Type Culture Collection (ATCC Acc. No: PTA-125146) on Jun. 27, 2018, in compliance with the Budapest Treaty.

Example 7

Imaging Human Amyloid Deposits in Mice

Human amyloid extracts from the heart (κ1), liver (κ1), spleen (λ1) and kidney (λ6) were kindly provided by Tufts University. Lyophilized human amyloid extracts were suspended in 25 ml of sterile PBS and homogenized for 3 minutes and centrifuged at 12,000 g for 30 minutes. 100 mg of the resulting pellet was resuspended in sterile saline. Balb/c mice were then injected subcutaneously with amyloid extract.

[$^{124}$I]CAEL-101:

cGMP grade CAEL-101 was radiolabeled with $^{124}$I, a positron emitting radioisotope used for PET imaging, with the standard iodegen reaction. (Fraker, et al.—*Biochem Biophys Res Commun* 80(4): 849-57; Markwell et al.—*Biochem* 17:4807-17) Approximately 5 days after human amyloid extract was implanted to form subcutaneous amyloidomas, the mice were injected with 50-200 µCi of [$^{124}$I] CAEL-101 and imaged up to 14 days post injection using an Inveon microPET scanner. SUVmax for amyloidomas and contralateral background were obtained by drawing regions of interest in the PMOD software package and calculating tumor-to-background (amyloid deposit-to-background) (T:B) ratios at 1 and 4 days post tracer infusion.

Figure 9:
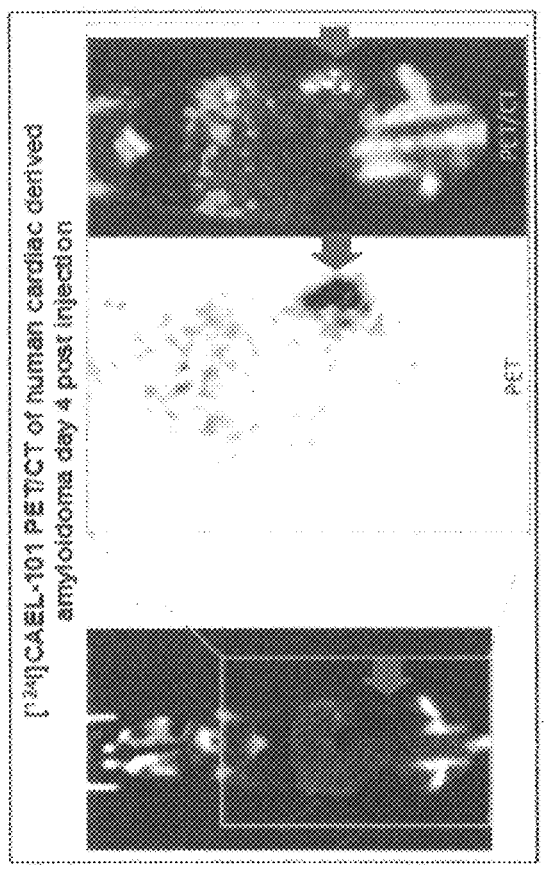
FIG. 9 is a PET image of a mouse implanted with human cardiac derived amyloidoma which was injected with [$^{124}I$] CAEL-101 and imaged at day 4 after injection.

[$^{124}$I]CAEL-101 successfully imaged 100% of mice bearing human amyloid extracts (κ1, λ1 and λ6 subtypes derived from heart, liver, spleen, and kidney). We demonstrated for the first time imaging of cardiac derived amyloidosis (shown in FIG. 9), which was reported to not work in prior literature. (Wall, et al.—*Blood*. 2010 116:2241). Human amyloidomas were visualized at both 1 and 4 days post tracer infusion, with significantly increasing T:B ratio by day 4. T:B ratios ranged from 2.1 to 4.2 at 4 days. We found heterogeneous uptake among various amyloidomas. For example, mice implanted with κ subtypes demonstrated significantly better in vivo T:B ratios (4.1+/−0.20), compared to λ subtypes (2.8+/−0.46), although all amyloidomas exhibited T:B uptake >2.1, which would be clinically significant. In additional work, κ subtype amyloidomas demonstrated significantly better in vivo imaging (T:B of 6) compared to λ subtypes (T:B of 2) at day 4. There was significantly increased T:B on day 4 vs day 1. However, on day 7 only the lower binding λ subtype amyloidomas demonstrated improved uptake compared to day 4 (T:B of 6 from 2). In contrast, the higher binding κ subtypes demonstrated a dramatic decrease in T:B on day 7 and no longer demonstrated significant activity.

This result of heterogeneous uptake among the various amyloidomas supports using real time PET imaging to stratify patients for therapy with the chimeric or humanized antibody described herein as well as to determine the appropriate dose of the antibody therapy. That is, one may determine the dosing of a patient based on the detected uptake of the labeled antibody or antibody fragment. A patient showing strong uptake (affinity) for the labeled antibody or antibody fragment may require a smaller amount of therapeutic antibody or antibody fragment than a patient showing a weaker uptake (affinity) for the labeled antibody or antibody fragment. The present disclosure therefore provides a method of determining the appropriate dosage of the disclosed humanized or chimeric antibody for therapy comprising the steps of administering to the patient a labeled antibody or antibody fragment disclosed herein, determining the uptake of the labeled antibody or antibody fragment by the amyloid deposits of the patient, and administering a dose or series of doses of chimeric or humanized antibody or antibody fragment to the patient based on the determined amount of uptake of the labeled antibody or antibody fragment.

[$^{89}$Zr]CAEL-101:

Although [$^{124}$I]CAEL-101 demonstrated significant binding to amyloidamas, the $^{124}$I radiolabel dehalogenates, causing much of the detected activity to be in the thyroid or untargeted (if thyroid is blocked). We therefore sought a method to radiolabel with a more stable radioisotope that can be imaged after blood clearance of unbound radiolabel (7-10 days). We radiolabeled CAEL-101 with 89-Zirconium ($^{89}$Zr), using two different strategies to create [$^{89}$Zr]-CAEL-101. One strategy employed the standard NCS linker that binds to random lysines on an antibody. (Eur J Nucl Mol Imaging. 2010 February 37(2): 250-59; Curr Radiopharm. 2011 Apr. 1; 4(2): 131-139) This method is used in many clinical applications but has been shown to create multiple radioisomers that can theoretically alter binding or biodistribution between batches. We therefore also radiolabeled CAEL-101 using a site specific approach that targets cystienes using the bifunctional deferoxamine-maleimide cross linker. (Nuclear Medicine and Biology 37 (2010) 289-297) Approximately 5 days after human cardiac amyloid extract was implanted to form subcutaneous amyloidomas, animals were injected with 50-200 µCi of [$^{89}$Zr]CAEL-101 and imaged 1, 4, 7, 11 and 14 days post injection using an Inveon microPET scanner.

Both variants of [$^{89}$Zr]CAEL-101 successfully imaged mice bearing cardiac amyloid extracts. They retained their immunoreactivity and demonstrated superior T:B compared to [$^{124}$I]CAEL-101 (18:1 vs 6:1). Furthermore, there was an actual increased T:B at day 7 in the higher binding κ subtype after [$^{89}$Zr]CAEL-101 injection, in contrast to the significant decrease seen with [$^{124}$I]CAEL-101. Human amyloidomas were visualized very well throughout the entire term of the experiment (14 days post tracer injection) with no evidence of significant breakdown of radiotracer. This is in contrast to what we found with the [$^{124}$I]CAEL-101 that had significantly broken down by day 4 and 7. This long duration of imaging of amyloid deposits enables one to use this labeled antibody for imaging deposits after significant blood clearance of unbound labeled antibody, which improves tumor-to-background (amyloid deposit-to-background) ratios and is important for imaging disease in organs that have high adjacent blood compartments, such as cardiac amyloid deposition. We found long term in vivo stability of the antibody binding component as we observed amyloidoma even 14 days after tracer injection. We again demonstrated imaging of cardiac derived amyloidosis, which had been reported to not work in prior literature. We observed for the first time ipsilateral uptake in lymphatic tissue, likely caused by amyloid in immune cells after phagocytosis migrating to draining nodes, possibly due to the fact that we implanted the amyloidomas in immunocompetent mice. This model undergoes spontaneous amyloid clearance due to the presence of human amyloid. This novel observation may provide a basis for a method of imaging response to therapy by looking for PET tracer uptake in lymph nodes.

In the description and claims of this specification the word "comprise" and variations of that word, such as "comprises" and "comprising" are not intended to exclude other features, additives, components, integers or steps but rather, unless otherwise stated explicitly, the scope of these words should be construed broadly such that they have an inclusive meaning rather than an exclusive one.

Although the compositions and methods of the invention have been described in the present disclosure by way of illustrative examples, it is to be understood that the invention is not limited thereto and that variations can be made as known by those skilled in the art without departing from the teachings of the invention defined by the appended claims.

What is claimed is:

1. An in vivo method of detecting the presence, location and/or quantity of cardiac-derived AL amyloid deposits in a patient suspected of having AL amyloid deposits comprising:
   administering to the patient a chimeric antibody having a detectable label linked thereto, the antibody comprising: a variable heavy chain (VH) comprising SEQ ID NO: 48; and a variable light chain (VK) comprising SEQ ID NO: 47; and
   detecting the presence, location, and/or quantity of cardiac-derived AL amyloid deposits by detecting the detectable label bound to the cardiac-derived AL amyloid deposits by diagnostic imaging,
   wherein the antibody is detectable at least at 7 days post administration, thereby detecting the presence, location and/or quantity of cardiac-derived AL amyloid deposits.

2. The method of claim 1 wherein the method of detection is positron emission spectroscopy (PET).

3. The method of claim 2, wherein the antibody is detectable at 14 days post administration.

4. The method of claim 3, wherein the detectable label is $^{89}$Zr.

5. The method of claim 4 wherein the antibody has a binding region with the same specificity as an antibody produced by a hybridoma cell line deposited as ATCC accession number PTA-105.

6. The method of claim 4 wherein the antibody has a binding region with the same specificity as an antibody produced by a cell line deposited as ATCC accession number PTA125146.

7. The method of claim 3 wherein the antibody has a binding region with the same specificity as an antibody produced by a hybridoma cell line deposited as ATCC accession number PTA-105.

8. The method of claim 3 wherein the antibody has a binding region with the same specificity as an antibody produced by a cell line deposited as ATCC accession number PTA125146.

9. The method of claim 1, wherein the cardiac-derived AL amyloid deposits are around the heart.

10. A composition for detecting the presence, location, and/or quantity of cardiac-derived AL amyloid deposits in a subject comprising a chimeric antibody having a detectable label linked thereto, the antibody comprising: a variable heavy chain (VH) comprising SEQ ID NO: 48; and a variable light chain (VK) comprising SEQ ID NO: 47, wherein the antibody is detectable for at least 7 days.

11. The composition of claim 10, wherein the antibody is detectable for 14 days.

12. The composition of claim 11, wherein the detectable label is $^{89}$Zr.

13. The composition of claim 12 wherein the antibody has a binding region with the same specificity as an antibody produced by a hybridoma cell line deposited as ATCC accession number PTA-105.

14. The composition of claim 12 wherein the antibody has a binding region with the same specificity as an antibody produced by a cell line deposited as ATCC accession number PTA125146.

15. The composition of claim 11 wherein the antibody has a binding region with the same specificity as an antibody produced by a hybridoma cell line deposited as ATCC accession number PTA-105.

16. The composition of claim 11 wherein the antibody has a binding region with the same specificity as an antibody produced by a cell line deposited as ATCC accession number PTA125146.

17. A method of monitoring disease progression in a patient diagnosed with an AL amyloid deposition disease and having cardiac-derived AL amyloid deposits comprising:
   a) administering to said patient the composition of claim 10 and conducting diagnostic imaging on the patient to detect the amount of detectable label bound to the cardiac-derived AL amyloid deposits,
   b) treating the patient with a therapy intended to remove AL amyloid deposits,
   c) administering to said patient the composition of claim 10,
   d) conducting diagnostic imaging on the patient to detect the amount of detectable label bound to the cardiac-derived AL amyloid deposits, and
   e) comparing the detected amount of detectable label in step d to the detected amount of detectable label in step a),
thereby monitoring disease progression.

18. The method of claim 17, wherein the patient is treated with humanized or chimeric 11-1F4 antibody or antigen-binding fragment thereof.

19. The method of claim 17, wherein the method of detection is PET.

20. The method of claim 17 wherein the antibody is detectable for 14 days.

21. The method of claim 20, wherein the detectable label is $^{89}$Zr.

22. The method of claim 21 wherein the antibody has a binding region with the same specificity as an antibody produced by a hybridoma cell line deposited as ATCC accession number PTA-105.

23. The method of claim 21 wherein the antibody has a binding region with the same specificity as an antibody produced by a cell line deposited as ATCC accession number PTA125146.

24. The method of claim 20 wherein the antibody has a binding region with the same specificity as an antibody produced by a hybridoma cell line deposited as ATCC accession number PTA-105.

25. The method of claim 20 wherein the antibody has a binding region with the same specificity as an antibody produced by a cell line deposited as ATCC accession number PTA125146.

26. The method of claim 17, wherein the cardiac-derived AL amyloid deposits are around the heart.

27. A method of determining the effectiveness of treatment to remove cardiac-derived AL amyloid deposits in a patient comprising:
   a) treating the patient with a therapeutically-effective dose of a chimeric 11-1F4 antibody or antigen-binding fragment thereof,
   b) administering to the patient a diagnostically-effective amount of the diagnostic composition of claim 10, and
   c) measuring by diagnostic imaging the amount of detectable molecule label from the diagnostic composition in the lymph nodes of the patient, wherein the higher the amount of detectable label detected in the lymph nodes, the more effective the treatment, thereby determining the effectiveness of the treatment.

28. The method of claim 27, wherein the cardiac-derived AL amyloid deposits are around the heart.

29. A method of determining the effectiveness of treatment to remove cardiac-derived AL amyloid deposits in a patient comprising:
   a) treating the patient with a therapeutically-effective dose of CAEL-101 or antigen-binding fragment thereof,
   b) administering to the patient a diagnostically-effective amount of the diagnostic composition of claim 10, and
   c) measuring by diagnostic imaging the amount of detectable label from the diagnostic composition in the lymph nodes of the patient,
wherein the higher the amount of detectable label detected in the lymph nodes, the more effective the treatment, thereby determining the effectiveness of the treatment.

30. The method of claim 29, wherein the cardiac-derived AL amyloid deposits are around the heart.

31. The composition of claim 10, wherein the cardiac-derived AL amyloid deposits are around the heart.

* * * * *

SEQUENCE LISTING

<160> NUMBER OF SEQ ID NOS: 54

<210> SEQ ID NO 1
<211> LENGTH: 31
<212> TYPE: DNA
<213> ORGANISM: Mus musculus

<400> SEQUENCE: 1
atgaagattg cctgttaggc tgttggtgct g                            31

<210> SEQ ID NO 2
<211> LENGTH: 31
<212> TYPE: DNA
<213> ORGANISM: Mus musculus

<400> SEQUENCE: 2
atggagwcag acacactccc tgytatgggt g                            31

<210> SEQ ID NO 3

<210> SEQ ID NO 3
<211> LENGTH: 30
<212> TYPE: DNA
<213> ORGANISM: Mus musculus

<400> SEQUENCE: 3
atgagtgtgc tcactcaggt cctggsgttg                                          30

<210> SEQ ID NO 4
<211> LENGTH: 33
<212> TYPE: DNA
<213> ORGANISM: Mus musculus

<400> SEQUENCE: 4
atgaggrccc ctgctcagwt tyttggmwtc ttg                                      33

<210> SEQ ID NO 5
<211> LENGTH: 30
<212> TYPE: DNA
<213> ORGANISM: Mus musculus

<400> SEQUENCE: 5
atggatttwc aggtgcagat twtcagcttc                                          30

<210> SEQ ID NO 6
<211> LENGTH: 29
<212> TYPE: DNA
<213> ORGANISM: mus musculus

<400> SEQUENCE: 6
atgaggtkcy ytgytsayct yctctgrgg                                           29

<210> SEQ ID NO 7
<211> LENGTH: 32
<212> TYPE: DNA
<213> ORGANISM: Mus musculus

<400> SEQUENCE: 7
atgggcwtca aagatggagt cacakwyycw gg                                       32

<210> SEQ ID NO 8
<211> LENGTH: 31
<212> TYPE: DNA
<213> ORGANISM: Mus musculus

<400> SEQUENCE: 8
atgtggggay ctkttttycm mttttttcaat g                                       31

<210> SEQ ID NO 9
<211> LENGTH: 25
<212> TYPE: DNA
<213> ORGANISM: Mus musculus

<400> SEQUENCE: 9
atggtrtccw casctcagtt ccttg                                               25

<210> SEQ ID NO 10
<211> LENGTH: 27
<212> TYPE: DNA
<213> ORGANISM: Mus musculus

<400> SEQUENCE: 10
atgtatatat gtttgttgtc tatttct                                             27

```
<210> SEQ ID NO 11
<211> LENGTH: 28
<212> TYPE: DNA
<213> ORGANISM: Mus musculus

<400> SEQUENCE: 11
atggaagccc cagctcagct tctcttcc                                    28

<210> SEQ ID NO 12
<211> LENGTH: 20
<212> TYPE: DNA
<213> ORGANISM: Mus musculus

<400> SEQUENCE: 12
actggatggt gggaagatgg                                             20

<210> SEQ ID NO 13
<211> LENGTH: 27
<212> TYPE: DNA
<213> ORGANISM: Mus musculus

<400> SEQUENCE: 13
atgaaatgca gctggggcat sttcttc                                     27

<210> SEQ ID NO 14
<211> LENGTH: 26
<212> TYPE: DNA
<213> ORGANISM: Mus musculus

<400> SEQUENCE: 14
atgggatgga gctrtatcat sytctt                                      26

<210> SEQ ID NO 15
<211> LENGTH: 27
<212> TYPE: DNA
<213> ORGANISM: Mus musculus

<400> SEQUENCE: 15
atgaagwtgt ggttaaactg ggttttt                                     27

<210> SEQ ID NO 16
<211> LENGTH: 25
<212> TYPE: DNA
<213> ORGANISM: Mus musculus

<400> SEQUENCE: 16
atgractttg ggytcagctt grttt                                       25

<210> SEQ ID NO 17
<211> LENGTH: 32
<212> TYPE: DNA
<213> ORGANISM: Mus musculus

<400> SEQUENCE: 17
atgggactcc aggcttcaat ttagttttcc tt                               32

<210> SEQ ID NO 18
<211> LENGTH: 29
<212> TYPE: DNA
<213> ORGANISM: Mus musculus

<400> SEQUENCE: 18
atggcttgtc yttrgsgctr ctcttctgc                                   29
```

```
<210> SEQ ID NO 19
<211> LENGTH: 27
<212> TYPE: DNA
<213> ORGANISM: Mus musculus

<400> SEQUENCE: 19
atggratgga gckggrgtct ttmtctt                                27

<210> SEQ ID NO 20
<211> LENGTH: 23
<212> TYPE: DNA
<213> ORGANISM: Mus musculus

<400> SEQUENCE: 20
atgagagtgc tgattctttt gtc                                   23

<210> SEQ ID NO 21
<211> LENGTH: 31
<212> TYPE: DNA
<213> ORGANISM: Mus musculus

<400> SEQUENCE: 21
atggmttggg tgtggamctt gcttattcct g                          31

<210> SEQ ID NO 22
<211> LENGTH: 28
<212> TYPE: DNA
<213> ORGANISM: Mus musculus

<400> SEQUENCE: 22
atgggcagac ttaccattct cattcctg                              28

<210> SEQ ID NO 23
<211> LENGTH: 28
<212> TYPE: DNA
<213> ORGANISM: Mus musculus

<400> SEQUENCE: 23
atggattttg ggctgatttt ttttattg                              28

<210> SEQ ID NO 24
<211> LENGTH: 27
<212> TYPE: DNA
<213> ORGANISM: Mus musculus

<400> SEQUENCE: 24
atgatggtgt taagtcttct gtacctg                               27

<210> SEQ ID NO 25
<211> LENGTH: 21
<212> TYPE: DNA
<213> ORGANISM: Mus musculus

<400> SEQUENCE: 25
cagtggatag acagatgggg g                                     21

<210> SEQ ID NO 26
<211> LENGTH: 21
<212> TYPE: DNA
<213> ORGANISM: Mus musculus

<400> SEQUENCE: 26
cagtggatag accgatgggg g                                     21
```

<210> SEQ ID NO 27
<211> LENGTH: 21
<212> TYPE: DNA
<213> ORGANISM: Mus musculus

<400> SEQUENCE: 27
cagtggatga gctgatgggg g							21

<210> SEQ ID NO 28
<211> LENGTH: 21
<212> TYPE: DNA
<213> ORGANISM: Mus musculus

<400> SEQUENCE: 28
caagggatag acagatgggg c							21

<210> SEQ ID NO 29
<211> LENGTH: 17
<212> TYPE: DNA
<213> ORGANISM: Artificial Sequence
<220> FEATURE:
<223> OTHER INFORMATION: The sequence contains sequences from Homo
      sapiens and Mus musculus

<400> SEQUENCE: 29
gttttcccag tcacgac							17

<210> SEQ ID NO 30
<211> LENGTH: 21
<212> TYPE: DNA
<213> ORGANISM: Artificial Sequence
<220> FEATURE:
<223> OTHER INFORMATION: The sequence contains sequences from Homo
      sapiens and Mus musculus

<400> SEQUENCE: 30
agcggataat ttcacacagg a							21

<210> SEQ ID NO 31
<211> LENGTH: 42
<212> TYPE: DNA
<213> ORGANISM: Artificial Sequence
<220> FEATURE:
<223> OTHER INFORMATION: The sequence contains sequences from Homo
      sapiens and Mus musculus

<400> SEQUENCE: 31
aagcttgccg ccaccatggc tgtcctgggg ctgctcttct gc							42

<210> SEQ ID NO 32
<211> LENGTH: 46
<212> TYPE: DNA
<213> ORGANISM: Artificial Sequence
<220> FEATURE:
<223> OTHER INFORMATION: The sequence contains sequences from Homo
      sapiens and Mus musculus

<400> SEQUENCE: 32
ccgatgggcc cttggtggag gctgaggaga cggtgactga ggttcc							46

<210> SEQ ID NO 33
<211> LENGTH: 43
<212> TYPE: DNA
<213> ORGANISM: Artificial Sequence
<220> FEATURE:

```
<223> OTHER INFORMATION: The sequence contains sequences from Homo
      sapiens and Mus musculus

<400> SEQUENCE: 33
aagcttgccg ccaccatgaa gttgcctgtt aggctgttgg tgc                              43

<210> SEQ ID NO 34
<211> LENGTH: 42
<212> TYPE: DNA
<213> ORGANISM: Artificial Sequence
<220> FEATURE:
<223> OTHER INFORMATION: The sequence contains sequences from Homo
      sapiens and Mus musculus

<400> SEQUENCE: 34
ggatccactc acgtttgatt tccagcttgg tccccctcc ga                               42

<210> SEQ ID NO 35
<211> LENGTH: 111
<212> TYPE: PRT
<213> ORGANISM: Mus musculus

<400> SEQUENCE: 35

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr Lys Pro Asn Leu Met
    50                  55                  60

Ser Arg Leu Ser Ile Ser Lys Asp Ile Ser Lys Ser Gln Val Leu Phe
65                  70                  75                  80

Lys Leu Asn Ser Leu Gln Thr Asp Asp Thr Ala Thr Tyr Tyr Cys Val
                85                  90                  95

Thr Leu Asp Tyr Trp Gly Gln Gly Thr Ser Val Thr Val Ser Ser
            100                 105                 110

<210> SEQ ID NO 36
<211> LENGTH: 112
<212> TYPE: PRT
<213> ORGANISM: Mus musculus

<400> SEQUENCE: 36

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Phe Gln Thr
                85                  90                  95

Thr Tyr Val Pro Asn Thr Phe Gly Gly Gly Thr Lys Leu Glu Ile Lys
            100                 105                 110
```

```
<210> SEQ ID NO 37
<211> LENGTH: 131
<212> TYPE: PRT
<213> ORGANISM: Artificial Sequence
<220> FEATURE:
<223> OTHER INFORMATION: The sequence contains sequences from Homo
      sapiens and Mus musculus

<400> SEQUENCE: 37

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Arg Asp Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
            100                 105                 110

Phe Gln Thr Thr Tyr Val Pro Asn Thr Phe Gly Gly Gly Thr Lys Leu
        115                 120                 125

Glu Ile Lys
    130

<210> SEQ ID NO 38
<211> LENGTH: 130
<212> TYPE: PRT
<213> ORGANISM: Artificial Sequence
<220> FEATURE:
<223> OTHER INFORMATION: The sequence contains sequences from Homo
      sapiens and Mus musculus

<400> SEQUENCE: 38

Met Ala Val Leu Gly Leu Leu Phe Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Ser Ser Tyr Gly Val Ser Trp Val Arg Gln Pro Pro Gly Lys Gly Leu
    50                  55                  60

Glu Trp Leu Gly Val Ile Trp Gly Asp Gly Ser Thr Asn Tyr His Pro
65                  70                  75                  80

Asn Leu Met Ser Arg Leu Ser Ile Ser Lys Asp Ile Ser Lys Ser Gln
                85                  90                  95

Val Leu Phe Lys Leu Asn Ser Leu Gln Thr Asp Asp Thr Ala Thr Tyr
            100                 105                 110

Tyr Cys Val Thr Leu Asp Tyr Trp Gly Gln Gly Thr Ser Val Thr Val
        115                 120                 125

Ser Ser
    130

<210> SEQ ID NO 39
<211> LENGTH: 333
<212> TYPE: DNA
```

<213> ORGANISM: Mus musculus

<400> SEQUENCE: 39

| | | |
|---|---|---|
| caggtgcagc tgaaggagtc aggacctggc ctggtggcgc cctcacagag cctgtccatc | 60 |
| acatgcactg tctcagggtt ctcattaagc agctatggtg taagctgggt tcgccagcct | 120 |
| ccaggaaagg gtctggagtg gctgggagta atatggggtg acgggagcac aaattatcat | 180 |
| ccaaatctca tgtccagact gagtatcagc aaggatattt ccaagagcca agttctcttc | 240 |
| aaactgaata gtctgcaaac tgatgacaca gccacgtact actgtgtcac cttcgactac | 300 |
| tggggtcaag gaacctcagt caccgtctcc tca | 333 |

<210> SEQ ID NO 40
<211> LENGTH: 336
<212> TYPE: DNA
<213> ORGANISM: Mus musculus

<400> SEQUENCE: 40

| | | |
|---|---|---|
| gatgttgtga tgacccaaac tccactctcc ctgcctgtca gtcttggaga tcaagcctcc | 60 |
| atctcttgca gatctagtca gagccttgta catagaaatg gaaacaccta tttacattgg | 120 |
| tacctgcaga agccaggcca gtctccaaag ctcctgatct acaaagtttc caaccgattt | 180 |
| tctggggtcc cagacaggtt cagtggcagt ggatcaggga cagatttcac actcaagatc | 240 |
| agcagagtgg aggctgagga tttgggactt tatttctgtt ttcaaactac atatgttccg | 300 |
| aacacgttcg gagggggac caagctggaa ataaaa | 336 |

<210> SEQ ID NO 41
<211> LENGTH: 43
<212> TYPE: DNA
<213> ORGANISM: Mus musculus

<400> SEQUENCE: 41

| | | |
|---|---|---|
| aagcttgccg ccaccatgaa gttgcctgtt aggctgttgg tgc | 43 |

<210> SEQ ID NO 42
<211> LENGTH: 422
<212> TYPE: DNA
<213> ORGANISM: Artificial Sequence
<220> FEATURE:
<223> OTHER INFORMATION: The sequence contains sequences from Homo
      sapiens and Mus musculus

<400> SEQUENCE: 42

| | | |
|---|---|---|
| aagcttgccg ccaccatgaa gttgcctgtt aggctgttgg tgctgatgtt ctggattcct | 60 |
| gcttccagca gtgatgttgt gatgacccaa actccactct ccctgcctgt cagtcttgga | 120 |
| gatcaagcct ccatctcttg cagatctagt cagagccttg tacatagaaa tggaaacacc | 180 |
| tatttacatt ggtacctgca gaagccaggc cagtctccaa agctcctgat ctacaaagtt | 240 |
| tccaaccgat tttctggggt cccagacagg ttcagtggca gtggatcagg gacagatttc | 300 |
| acactcaaga tcagcagagt ggaggctgag gatttgggac tttatttctg ttttcaagac | 360 |
| tacatatgtt ccgaacacgt tcggaggggg gaccaagctg gaaatcaaac gtgagtggat | 420 |
| cc | 422 |

<210> SEQ ID NO 43
<211> LENGTH: 42
<212> TYPE: DNA
<213> ORGANISM: Mus musculus

<400> SEQUENCE: 43
ggatccactc acgtttgatt tccagcttgg tcccccctcc ga    42

<210> SEQ ID NO 44
<211> LENGTH: 42
<212> TYPE: DNA
<213> ORGANISM: Mus musculus

<400> SEQUENCE: 44
aagctttccg ccaccatggc tgtcctgggg ctgctcttct gc    42

<210> SEQ ID NO 45
<211> LENGTH: 426
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 45
aagctttccg ccaccatggc tgtcctgggg ctgctcttc tgcctggtga cattaccaag    60
ctgtgtcctg tcccaggtgc agctgaagga gtcaggacct ggcctggtgg agcctcacag   120
agcctgtcca tcacatgcac tgtctcaggg ttctcattaa gcagctatgg tgtaagctgg   180
gttcgccagc ccaggaaagg gtctggagtg gctgggagta atatggggtg acggagcac   240
aaattatcat ccaaatctca tgtccagact gagtatcagc aaggatattt ccaagagcaa   300
gttctcttca aactgaatag tctgcaaact gatgacacag ccacgtacta ctgtgtcacc   360
ttggactact ggggtcaaag gaacctccag tcaccgtctc ctcagcctcc accacgggcc   420
catcgg   426

<210> SEQ ID NO 46
<211> LENGTH: 46
<212> TYPE: DNA
<213> ORGANISM: Mus musculus

<400> SEQUENCE: 46
ccgatgggcc cttggtggag gctgaggaga cggtgactga ggttcc    46

<210> SEQ ID NO 47
<211> LENGTH: 112
<212> TYPE: PRT
<213> ORGANISM: Artificial Sequence
<220> FEATURE:
<223> OTHER INFORMATION: The sequence contains sequences from Homo sapiens and Mus musculus

<400> SEQUENCE: 47

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Arg Asp Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Phe Gln Thr
                85                  90                  95

Thr Tyr Val Pro Asn Thr Phe Gly Gly Gly Thr Lys Leu Glu Ile Lys
            100                 105                 110

<210> SEQ ID NO 48
<211> LENGTH: 111
<212> TYPE: PRT
<213> ORGANISM: Artificial Sequence
<220> FEATURE:
<223> OTHER INFORMATION: The sequence contains sequences from Homo
      sapiens and Mus musculus

<400> SEQUENCE: 48

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Asn Leu Met
    50                  55                  60

Ser Arg Leu Ser Ile Ser Lys Asp Ile Ser Lys Ser Gln Val Phe Leu
65                  70                  75                  80

Lys Leu Asn Ser Leu Gln Thr Asp Asp Thr Ala Thr Tyr Tyr Cys Val
                85                  90                  95

Thr Leu Asp Tyr Trp Gly Gln Gly Thr Ser Val Thr Val Ser Ser
            100                 105                 110

<210> SEQ ID NO 49
<211> LENGTH: 16
<212> TYPE: PRT
<213> ORGANISM: Artificial Sequence
<220> FEATURE:
<223> OTHER INFORMATION: Derived from Mus musculus

<400> SEQUENCE: 49

Arg Ser Ser Gln Ser Leu Val His Arg Asn Gly Asn Tyr Thr Leu His
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Derived from Mus muscalus

<400> SEQUENCE: 50

Leu Val Ser Asn Arg Phe Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Derived from Mus musculus

<400> SEQUENCE: 51

Phe Asn Thr Thr Tyr Val Pro Asn Thr
1               5

<210> SEQ ID NO 52
<211> LENGTH: 6
<212> TYPE: PRT

```
<213> ORGANISM: Artificial Sequence
<220> FEATURE:
<223> OTHER INFORMATION: Derived from Mus musculus

<400> SEQUENCE: 52

Ser Tyr Gly Val Ser Trp
1               5

<210> SEQ ID NO 53
<211> LENGTH: 21
<212> TYPE: PRT
<213> ORGANISM: Artificial Sequence
<220> FEATURE:
<223> OTHER INFORMATION: Derived from Mus musculus

<400> SEQUENCE: 53

Val Ile Trp Gly Asp Gly Ser Thr Asn Tyr His Pro Asn Leu Met Ser
1               5                   10                  15

Arg Leu Ser Ile Ser
            20

<210> SEQ ID NO 54
<211> LENGTH: 3
<212> TYPE: PRT
<213> ORGANISM: Artificial Sequence
<220> FEATURE:
<223> OTHER INFORMATION: Derived from Mus musculus

<400> SEQUENCE: 54

Leu Asp Tyr
1
```